(12) United States Patent
Belley et al.

(10) Patent No.: US 6,211,197 B1
(45) Date of Patent: Apr. 3, 2001

(54) PROSTAGLANDIN RECEPTOR LIGANDS

(75) Inventors: Michel Belley, Pierrefonds; Marc Labelle, Iie Perrot; Nicholas Lachance; Michel Gallant, both of Pierrefonds; Nathalie Chauret, Iie Bizard; Laird A. Trimble, Pierrefonds; Chun Li, Kirkland, all of (CA)

(73) Assignee: Merck Frosst Canada & Co., Kirkland (CA)

( * ) Notice: Subject to any disclaimer, the term of this patent is extended or adjusted under 35 U.S.C. 154(b) by 0 days.

(21) Appl. No.: 09/411,505

(22) Filed: Oct. 4, 1999

Related U.S. Application Data

(60) Provisional application No. 60/103,564, filed on Oct. 7, 1998.

(51) Int. Cl.$^7$ .................. A61K 31/192; A61K 31/47; C07C 59/66; C07D 215/14; C07D 257/04; A61P 29/00

(52) U.S. Cl. .............. 514/311; 514/363; 514/383; 514/445; 514/464; 514/469; 514/568; 514/576; 514/601; 514/602; 514/604; 514/605; 546/172; 546/174; 548/132; 548/252; 549/77; 549/469; 549/447; 562/41; 562/508; 562/510; 562/586; 562/567; 564/80; 564/87; 564/84; 564/91; 564/99

(58) Field of Search .................... 546/172, 174; 548/136, 252; 549/77, 469, 447; 562/41, 508, 510, 586, 567; 564/80, 87, 84, 91, 99; 514/311, 363, 383, 445, 464, 469, 568, 576, 601, 602, 604, 605

(56) References Cited

U.S. PATENT DOCUMENTS

| 3,641,133 | | 2/1972 | Galantay et al. . | |
|---|---|---|---|---|
| 3,780,061 | | 12/1973 | Allais et al. . | |
| 4,922,022 | | 5/1990 | Dixon et al. . | |
| 5,462,954 | * | 10/1995 | Baker | 514/381 |
| 5,495,046 | * | 2/1996 | Nakazato | 562/597 |

FOREIGN PATENT DOCUMENTS

| 407 101 | 2/1966 | (DE) . |
|---|---|---|
| WO 96/06822 | 3/1996 | (WO) . |

OTHER PUBLICATIONS

XP–000857564–Rekker, R. F., et al.Recueil Des Trav Aux Chimiques Des Pays–Bas, vol. 90, pp. 343–351, 1971.
XP–002126076–Springer, J. M., et al..—J. of Organic Chemistry, vol. 35, No. 5, pp. 1260–1264, 1970.

* cited by examiner

*Primary Examiner*—Evelyn Mei Huang
(74) *Attorney, Agent, or Firm*—Raynard Yuro; David L. Rose

(57) ABSTRACT

Compounds and methods for treating prostaglandin mediated diseases, and certain pharmaceutical compositions thereof are disclosed. The compounds are represented by formula II:

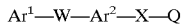

$$Ar^1—W—Ar^2—X—Q \qquad II$$

The compounds of the invention are structurally different from NSAIDs and opiates, and are antagonists of the pain and inflammatory effects of E-type prostaglandins.

12 Claims, No Drawings

PROSTAGLANDIN RECEPTOR LIGANDS

CROSS REFERENCE TO RELATED APPLICATIONS

This application is a non-provisional application related to U.S. application Ser. No. 60/103,564 filed on Oct. 7, 1998 priority of which is claimed hereunder.

BACKGROUND OF THE INVENTION

This invention relates to compounds and methods for treating prostaglandin mediated diseases, and certain pharmaceutical compositions thereof. More particularly, the compounds of the invention are structurally different from NSAIDs and opiates, and are antagonists of the pain and inflammatory effects of E-type prostaglandins.

Two review articles describe the characterization and therapeutic relevance of the prostanoid receptors as well as the most commonly used selective agonists and antagonists: *Eicosanoids: From Biotechnology to Therapeutic Applications*, Folco, Samuelsson, Maclouf, and Velo eds, Plenum Press, New York, 1996, chap. 14, 137–154 and Journal of Lipid Mediators and Cell Signalling, 1996, 14, 83–87. An article from *The British Journal of Pharmacology* (1994, 112, 735–740) suggests that Prostaglandin $E_2$ ($PGE_2$) exerts allodynia through the $EP_1$ receptor subtype and hyperalgesia through $EP_2$ and $EP_3$ receptors in the mouse spinal cord.

Thus, selective prostaglandin ligands, agonists or antagonists, depending on which prostaglandin E receptor subtype is being considered, have anti-inflammatory, anti-pyretic and analgesic properties similar to a conventional non-steroidal anti-inflammatory drug, and in addition, inhibit hormone-induced uterine contractions and have anti-cancer effects. These compounds have a diminished ability to induce some of the mechanism-based side effects of NSAIDs which are indiscriminate cyclooxygenase inhibitors. In particular, the compounds have a reduced potential for gastrointestinal toxicity, a reduced potential for renal side effects, a reduced effect on bleeding times and a lessened ability to induce asthma attacks in aspirin-sensitive asthmatic subjects.

PCT application nos WO 96/06822 (Mar. 7, 1996), WO 96/11902 (Apr. 25, 1996), WO 97/00863 (Jan. 9, 1997), WO 97/00864 (Jan. 9, 1997), WO 96/03380 (Feb. 8, 1996), and EP 752421-A1 (Jan. 8, 1997) disclose compounds represented by Formula I as being useful in the treatment of prostaglandin mediated diseases.

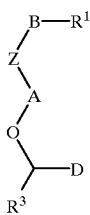

I

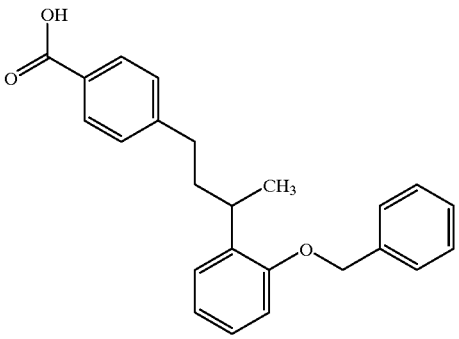

Ia wherein:
A is phenyl, naphthyl, 5- or 6-membered heteroaryl
B is phenyl, 5- or 6-membered heteroaryl or a further defined keto-dihydro ring;
D is phenyl, 5- or 6-membered heteroaryl;
$R^1$ is COOH, carboxyalkyl, tetrazolyl(alkyl);
$R^3$ is H or alkyl, and
Z is an alkylene bridge containing 0–1 nitrogen atom or a further defined unsaturated bridge.

Compound Ia is one of the compounds specifically claimed.

SUMMARY OF THE INVENTION

The present invention relates to compounds represented by formula II:

$$Ar^1\text{—}W\text{—}Ar^2\text{—}X\text{—}Q \qquad \text{II}$$

as well as pharmaceutically acceptable salts and hydrates thereof, wherein:
$Ar^1$ is an aryl or heteroaryl group, optionally substituted with $R^1$ or $R^3$;
$R^1$ is $Y_m\text{—}R^2$, $Y_m\text{—}Ar^3$, halogen, $N(R^5)_2$, CN, $NO_2$, $C(R^6)_3$, $CON(R^5)_2$, $S(O)_nR^7$ or OH;
Y represents a linker between $R^2$ or $Ar^3$ and $Ar^1$ containing 0–4 carbon atoms and not more than one heteroatom selected from O, N and S, said linker optionally containing CO, $S(O)_n$, —C=C— or an acetylenic group, and said linker being optionally substituted by $R^2$;
m is 0 or 1;
n is 0, or 2;
$R^2$ represents H, F, $CHF_2$, $CF_3$, lower alkyl or hydroxy$C_{1-6}$ alkyl, or two $R^2$ groups may be joined together and represent a carbocyclic ring of up to six members, said ring containing not more than one heteroatom selected from O, N and S;
$Ar^3$ represents an aryl or heteroaryl group, optionally substituted with $R^3$;
$R^3$ is $R^4$, halogen, halo$C_{1-6}$alkyl, $N(Rr)_2$, CN, $NO_2$, $C(R^6)_3$, $CON(R^5)_2$, $OR^4$, $SR^4$ or $S(O)_nR^7$;
$R^4$ is H, lower alkyl, lower alkenyl, lower alkynyl, $CHF_2$ or $CF_3$;
$R^5$ is $R^4$, Ph or Bn, or two $R^5$ groups in combination with the atom to which they are attached represent a ring of up to 6 members containing carbon atoms and up to 2 heteroatoms selected from O, N and S;
$R^6$ is H, F, $CF_3$ or lower alkyl, or two $R^6$ groups may be taken together and represent a ring of up to 6 members containing carbon atoms and 0–2 heteroatoms selected from O, N and S;

$R^7$ is lower alkyl, lower alkenyl, lower alkynyl, $CHF_2$, $CF_3$, $N(R^5)_2$, $Ph(R^8)_2$ or $CH_2Ph(R^8)_2$;

$R^8$ is $R^4$, $OR^4$, $SR^4$ or halogen

W represents a 3–6 membered linking group containing 0 to 2 heteroatoms selected from O, N and S, said linking group optionally containing CO, $S(O)_n$, C=C or an acetylenic group, and optionally being substituted with $R^9$;

$R^9$ is $R^2$, lower alkenyl, lower alkynyl, $OR^4$ or $SR^4$;

$Ar^2$ represents an aryl or heteroaryl group, optionally ubstituted with $R^3$;

$R^{10}$ represents $R^4$, halogen, $N(R^5)_2$, CN, $NO_2$, $C(R^6)_3$, $OR^4$, $SR^4$ or $S(O)_nR^7$;

X represents a linker which is attached to $Ar^2$ ortho to the attachment of W, said linker containing 0–4 carbon atoms and not more than one heteroatom selected from O, N and S, said linker further optionally containing CO, $S(O)_n$, C=C or an acetylenic group, and said linker being optionally substituted with $R^{11}$;

$R^{11}$ is $R^9$;

Q represents a member selected from the group consisting of: $CO_2H$, tetrazole, $SO_3H$, hydroxamic acid, $CONHSO_2R^{12}$ and $SO_2NHCOR^{12}$;

$R^{12}$ represents a member selected from the group consisting of: $CF_3$, lower alkyl, lower alkenyl, lower alkynyl and $ZAr^4$, wherein Z is an optional linker containing 0–4 carbon atoms, optionally substituted with $R^{13}$;

$R^{13}$ is $R^9$;

$Ar^4$ is an aryl or heteroaryl group optionally substituted with $R^{14}$, and $R^{14}$ is $R^{10}$ or NHCOMe.

Pharmaceutical compositions and methods of treatment are also included.

DETAILED DESCRIPTION OF THE INVENTION

The present invention relates to compounds represented by formula II:

$$Ar^1—W—Ar^2—X—Q \qquad II$$

as well as pharmaceutically acceptable salts and hydrates thereof, wherein:

$Ar^1$ is an aryl or heteroaryl group, optionally substituted with $R^1$ or $R^3$;

$R^1$ is $Y_m—R^2$, $Y_m—Ar^3$, halogen, $N(R^5)_2$, CN, $NO_2$, $C(R^6)_3$, $CON(R^5)_2$, $S(O)_nR^7$ or OH;

Y represents a linker between $R^2$ or $Ar^3$ and $Ar^1$ containing 0–4 carbon atoms and not more than one heteroatom selected from O, N and S, said linker optionally containing CO, $S(O)_n$, —C=C— or an acetylenic group, and said linker being optionally substituted by $R^2$;

m is 0 or 1;

n is 0, 1 or 2;

$R^2$ represents H, F, $CHF_2$, $CF_3$, lower alkyl or hydroxy$C_{1-6}$ alkyl, or two $R^2$ groups may be joined together and represent a carbocyclic ring of up to six members, said ring containing not more than one heteroatom selected from O, N and S;

$Ar^3$ represents an aryl or heteroaryl group, optionally substituted with $R^3$;

$R^3$ is $R^4$, halogen, halo$C_{1-6}$alkyl, $N(R^5)_2$, CN, $NO_2$, $C(R^6)_3$, $CON(R^5)_2$, $OR^4$, $SR^4$ or $S(O)_nR^7$;

$R^4$ is H, lower alkyl, lower alkenyl, lower alkynyl, $CHF_2$ or $CF_3$;

$R^5$ is $R^4$, Ph or Bn, or two $R^5$ groups in combination with the atom to which they are attached represent a ring of up to 6 members containing carbon atoms and up to 2 heteroatoms selected from O, N and S;

$R^6$ is H, F, $CF_3$ or lower alkyl, or two $R^6$ groups may be taken together and represent a ring of up to 6 members containing carbon atoms and 0–2 heteroatoms selected from O, N and S;

$R^7$ is lower alkyl, lower alkenyl, lower alkynyl, $CHF_2$, $CF_3$, $N(R^5)_2$, $Ph(R^8)_2$ or $CH_2Ph(R^8)_2$;

$R^8$ is $R^4$, $OR^4$, $SR^4$ or halogen

W represents a 3–6 membered linking group containing 0 to 2 heteroatoms selected from O, N and S, said linking group optionally containing CO, $S(O)_n$, C=C or an acetylenic group, and optionally being substituted with $R^9$;

$R^9$ is $R^2$, lower alkenyl, lower alkynyl, $OR^4$ or $SR^4$;

$Ar^2$ represents an aryl or heteroaryl group, optionally substituted with $R^3$;

$R^{10}$ represents $R^4$, halogen, $N(R^5)_2$, CN, $NO_2$, $C(R^6)_3$, $OR^4$, $SR^4$ or $S(O)_nR^7$;

X represents a linker which is attached to $Ar^2$ ortho to the attachment of W, said linker containing 0–4 carbon atoms and not more than one heteroatom selected from O, N and S, said linker further optionally containing CO, $S(O)_n$, C=C or an acetylenic group, and said linker being optionally substituted with $R^{11}$;

$R^{11}$ is $R^9$;

Q represents a member selected from the group consisting of: $CO_2H$, tetrazole, $SO_3H$, hydroxamic acid, $CONHSO_2R^{12}$ and $SO_2NHCOR^{12}$;

$R^{12}$ represents a member selected from the group consisting of: $CF_3$, lower alkyl, lower alkenyl, lower alkynyl and $ZAr^4$, wherein Z is an optional linker containing 0–4 carbon atoms, optionally substituted with $R^{13}$;

$R^{13}$ is $R^9$;

$Ar^4$ is an aryl or heteroaryl group optionally substituted with $R^{14}$, and $R^{14}$ is $R^{10}$ or NHCOMe.

As used herein, the following terms and definitions apply unless indicated otherwise.

The following abbreviations have the indicated meanings:

| | |
|---|---|
| Ac | = acetyl |
| AIBN | = 2,2'-azobisisobutyronitrile |
| Bn | = benzyl |
| DHP | = 2,3-dihydro-4H-pyran |
| DIBAL | = diisobutyl aluminum hydride |
| DIPHOS | = 1,2-bis(diphenylphosphino)ethane |
| DMAP | = 4-(dimethylamino)pyridine |
| DMF | = N,N-dimethylformamide |
| DMSO | = dimethyl sulfoxide |
| EDCI | = 1-(3-dimethylaminopropyl)-3-ethylcarbodiimide hydrochloride |
| $Et_3N$ | = triethylamine |
| Fur | = furandiyl |
| HBBS | = Hanks balanced salt solution |
| HEPES | = N-[2-hydroxyethyl]piperazine-N'-[2-ethanesulfonic acid] |

| | -continued |
|---|---|
| KHMDS = | potassium hexamethyldisilazane |
| LDA = | lithium diisopropylamide |
| LPS = | lipopolysaccharide |
| MCPBA = | metachloroperbenzoic acid |
| MES = | 2-[N-morpholino]ethanesulfonic acid |
| Ms = | methanesulfonyl = mesyl |
| MsO = | methanesulfonate = mesylate |
| NBS = | N-bromosuccinimide |
| NCS = | N-chlorosuccinimide |
| NSAID = | non-steroidal anti-inflammatory drug |
| PCC = | pyridinium chlorochromate |
| PDC = | pyridinium dichromate |
| Ph = | phenyl |
| Phe = | benzenediyl |
| PPTS = | pyridinium p-toluenesulfonate |
| pTSA = | p-toluenesulfonic acid |
| Pye = | pyridinediyl |
| r.t. = | room temperature |
| rac. = | racemic |
| Tf = | trifluoromethanesulfonyl = triflyl |
| TfO = | trifluoromethanesulfonate = triflate |
| Th = | 2- or 3-thienyl |
| THF = | tetrahydrofuran |
| Thi = | thiophenediyl |
| THP = | tetrahydropyran-2-yl |
| Thz = | thiazol-2-yl |
| TLC = | thin layer chromatography |
| Ts = | p-toluenesulfonyl = tosyl |
| TsO = | p-toluenesulfonate = tosylate |
| Tz = | 1H (or 2H)-tetrazol-5-yl |
| $C_3H_5$ = | allyl |

| Alkyl group abbreviations |  |
|---|---|
| Me = | methyl |
| Et = | ethyl |
| n-Pr = | normal propyl |
| i-Pr = | isopropyl |
| n-Bu = | normal butyl |
| i-Bu = | isobutyl |
| s-Bu = | secondary butyl |
| t-Bu = | tertiary butyl |
| c-Pr = | cyclopropyl |
| c-Bu = | cyclobutyl |
| c-Pen = | cyclopentyl |
| c-Hex = | cyclohexyl |

The terms alkyl, alkenyl, and alkynyl mean linear, branched, and cyclic structures and combinations thereof.

"Alkyl" and the alkyl portions of alkoxy, arylalkyl, alkylaryl and the like include "cycloalkyl" and "ower alkyl" and extends to cover carbon fragments having up to 20 carbon atoms. Examples of alkyl groups include octyl, nonyl, undecyl, dodecyl, tridecyl, tetradecyl, pentadecyl, eicosyl, 3,7-diethyl-2,2-dimethyl4-propylnonyl, and the like.

"Lower alkyl" includes "lower cycloalkyl" and means alkyl groups of from 1 to 7 carbon atoms. Examples of lower alkyl groups include methyl, ethyl, propyl, isopropyl, butyl, s- and t-butyl, pentyl, hexyl, heptyl, and the like.

"Cycloalkyl" includes "lower cycloalkyl" and means a hydrocarbon, containing one or more rings of from 3 to 12 carbon atoms, with the hydrocarbon having up to a total of 20 carbon atoms. Examples of cycloalkyl groups are cyclopropyl, cyclopentyl, cycloheptyl, adamantyl, cyclododecylmethyl, 2-ethyl-1-bicyclo[4.4.0]decyl, and the like.

"Lower cycloalkyl" means a hydrocarbon containing one or more rings of from 3 to 7 carbon atoms, with the hydrocarbon having up to a total of 7 carbon atoms. Examples of lower cycloalkyl groups are cyclopropyl, cyclopropylmethyl, cyclobutyl, 2-cyclopentylethyl, cycloheptyl, bicyclo[2.2.1]hept-2-yl, and the like.

The term "alkenyl" includes "cycloalkenyl" and "lower alkenyl" and means alkenyl groups of 2 to 20 carbon atoms. Examples of alkenyl groups include allyl, 5-decen-1-yl, 2-dodecen-1-yl, and the like.

"Lower alkenyl" includes "lower cycloalkenyl" and means alkenyl groups of 2 to 7 carbon atoms. Examples of lower alkenyl groups include vinyl, allyl, isopropenyl, pentenyl, hexenyl, heptenyl, 1-propenyl, 2-butenyl, 2-methyl-2-butenyl, and the like.

"Cycloalkenyl" includes "lower cycloalkenyl" and means alkenyl groups of 3 to 20 carbon atoms, which include a ring of 3 to 12 carbon atoms, and in which the alkenyl double bond may be located anywhere in the structure. Examples of cycloalkenyl groups are cyclopropen-1-yl, cyclohexen-3-yl, 2-vinyladamant-1-yl, 5-methylene-dodec-1-yl and the like.

"Lower cycloalkenyl" means alkenyl groups of 3 to 7 carbon atoms, which include a ring of 3 to 7 carbon atoms and in which the double bond may be located anywhere in the structure. Examples of lower cycloalkenyl groups are cyclopropen-1-yl, cyclohexen-3-yl, 2-cyclopentylethen-1-yl, and the like.

The term "alkynyl" includes "cycloalkynyl" and "lower alkynyl" and means alkynyl groups of 2 to 20 carbon atoms. Examples of alkynyl groups are ethynyl, 2-pentadecyn-1-yl, 1-eicosyn-1-yl, and the like.

"Lower alkynyl" includes "lower cycloalkynyl" and means alkynyl groups of 2 to 7 carbon atoms. Examples of lower alkynyl groups include ethynyl, propargyl, 3-methyl-1-pentynyl, 2-heptynyl and the like.

"Cycloalkynyl" includes "lower cycloalkynyl" and means alkynyl groups of 5 to 20 carbon atoms, which include a ring of 3 to 20 carbon atoms. The alkynyl triple bond may be located anywhere in the group, with the proviso that if it is within a ring, such a ring must be of 10 members or greater. Examples of cycloalkynyl are cyclododecyn-3-yl, 3-cyclohexyl-1-propyn-1-yl, and the like.

"Lower cycloalkynyl" means alkynyl groups of 5 to 7 carbon atoms which include a ring of 3 to 5 carbon atoms. Examples of lower cycloalkynyl are cyclopropylethynyl, 3-(cyclobutyl)-1-propynyl, and the like.

Halogen includes F, Cl, Br and I. When a group is "halogenated", it is substituted with one or more halogen atoms, up to the maximum number of positions available for substitution, i.e., it is "perhalogenated".

The definition of any substituent (e.g., $R^6$, $R^{10}$, etc.) in a particular molecule is independent of its definition elsewhere in the molecule. Thus, —N($R^5$)$_2$ represents —NHH, —NHCH$_3$, —NHC$_6$H$_5$, and the like.

Examples of rings formed when two R groups join include cyclopropane, cyclobutane, cyclopentane, cyclohexane, cycloheptane, oxetane, tetrahydrofuran, tetrahydropyran, tetrahydrothiophene, tetrahydrothiopyran, pyrrolidine and piperidine.

The heterocycles formed when two $R^5$ groups join through N include pyrrolidine, piperidine, morpholine, thiamorpholine, piperazine and N-methylpiperazine.

Aryl and the aryl portions of arylalkyl, aryloxy, arylalkoxy and the like refer to aromatic as well as partially aromatic 6–12 membered ring systems. Examples include benzene, naphthalene, biphenyl and tetrahydronaphthalene.

Heteroaryl and the heteroaryl portion of heteroarylalkyl, heteroarylalkoxy, heteroaryloxy and the like refer to 5–15 membered aromatic and partially aromatic ring systems, containing 1–4 heteroatoms selected from O, S and N. Examples include pyridine, quinoline, isoquinoline, furan, benzofuran, thiophene, benzothiophene, oxazole, thiazole, benzothiazole, 1,3,4-thiadiazole, thienopyridine, indole, tetrazole, imidazole, benzoxazole, pyrrole and methylenedioxyphenyl.

Haloaryl and haloheteroaryl refer to aryl and heteroaryl groups respectively having at least one halo atom attached, up to perhalogenated, as indicated above. Haloalkyl refers to alkyl groups which have one or more halogen atoms attached, including up to the maximum number of positions which can be substituted, i.e., perhalogenated alkyl groups. In haloalkylarylalkoxy, the terminal alkyl portion is halogenated. In haloarylalkoxy, the aryl portion is halogenated, and in haloheteroarylalkoxy the heteroaryl portion is halogenated.

Aryl, heteroaryl and other groups are termed optionally substituted as described herein. When a moiety is optionally substituted, this means that the moiety is unsubstituted or is substituted with 1–5 of the substituent groups, as permitted with respect to the availability for substitution. In particular, this applies to $Ar^1$, which is optionally substituted with 1–5 $R^1$ and/or $R^3$ groups. Y is optionally substituted with 1–5 $R^2$ groups. $Ar^3$ is optionally substituted with 1–5 $R^3$ groups. W is optionally substituted with 1–5 $R^9$ groups. $Ar^2$ is optionally substituted with 1–5 $R^3$ groups. X is optionally substituted with 1–5 $R^{11}$ groups. Z is optionally substituted with 1–5 $R^{13}$ groups, and $Ar^4$ is optionally substituted with 1–5 $R^{14}$ groups.

Y represents an optional linking group between $Ar^1$ and $R^2$ or $R^3$. When m is 0, Y is absent and when m is 1, Y is present. The linking group contains 0–4 carbon atoms and 0–1 heteroatoms selected from O, S and N, and further is optionally substituted with $R^2$. Examples of suitable linking groups include: O, S, $NR^2$, $OCH_2$, CH=CH, $SO_2CH_2$, $NHCHMeCH_2$,O, $CH_2$, $CH_2CH$=CH and the like.

W represents a 3–6 membered linking group containing 0 to 2 heteroatoms selected from O, N and S, said linking group optionally containing CO, $S(O)_n$, C=C or an acetylenic group, and optionally being substituted with $R^9$. Examples include $OCH_2CH_2$, CH=$CHCH_2$, $CH_2SO_2CH_2$, $NHCHMeCH_2$, $(CH_2)_5$, $CH_2CH$=$CHCH_2$, $O(CH_2)_3O$, $CH_2NHCO$, $CH_2C$+C, $CH_2OCH_2$, $CH_2CH$=CH, 1,2-c-Pr—$CH_2$, $CH_2$-1,2-c-Pr and the like.

X represents a linker that is attached to $Ar^2$ ortho to the attachment of W. The linker contains 0–4 carbon atoms and not more than one heteroatom selected from O, N and S. Linker X further optionally contains a group CO, $S(O)_n$, C=C or an acetylenic group, and said linker is optionally substituted with $R^{11}$. Examples of X include $OCH_2$, CH=CH, $SO_2CH_2$, $NHCHMeCH_2$,O, $CH_2$, $CH_2$ CH=CH, 1,2-c-Pr, $(CH_2)_2O$, C=C, and the like.

In $ZAr^4$, Z represents an optional linker having 0–4 carbon atoms, and being optionally substituted with $R^{13}$. Examples of such a linker include a bond, $CH_2CH_2$, CH=CH, $CHMeCH_2$, $CH_2$, $CH_2CH$=CH, 1,2-c-Pr, and the like.

One aspect of the invention that is of particular interest relates to compounds of formula II wherein $R^1$ is OH, $OCH_2Ar^3$, $SCH_2Ar^3$, $OAr^3$, $SAr^3$ or $NR^2CH_2Ar^3$. Within this subset, all other variables are as originally defined.

Another aspect of the invention that is of particular interest relates to compounds of formula II wherein $Ar^3$ is an aryl or heteroaryl group selected from the group consisting of benzene, pyridine, thiophene, furan, oxazole and thiazole, said group being optionally substituted with $R^3$. Within this subset, all other variables are as originally defined.

Another aspect of the invention that is of particular interest relates to compounds of formula II wherein $Ar^2$ is an aryl or heteroaryl group selected from the group consisting of: benzene, pyridine, thiophene, furan, oxazole and thiazole, said group being optionally substituted with 1–5 groups selected from $R^4$, $OR^4$, $SR^4$ and halogen.

Another aspect of the invention that is of particular interest relates to compounds of formula II wherein W is selected from the group consisting of: $CH_2OCH_2$, $(CH_2)_3$, $CH_2CH$=CH, CH=$CHCH_2$, CH(OH)CH=CH, CH=CHCH(OH), $CH_2C$≡C, C≡$CCH_2$, 1,2-c-Pr-$CH_2$ and -1,2-c-Pr—$CH_2$—. Within this subset, all other variables are as originally defined.

Another aspect of the invention that is of particular interest relates to compounds of formula II wherein X is selected from the group consisting of: $(CH_2)_2$, CH=CH, C≡C and 1,2-c-Pr. Within this subset, all other variables are as originally defined.

Another aspect of the invention that is of particular interest relates to compounds of formula II wherein Q is $CO_2H$ or tetrazole. Within this subset, all other variables are as originally defined.

Another aspect of the invention that is of particular interest relates to compounds of formula II wherein Z represents a 0–2 carbon atom linker that is unsubstituted. Within this subset, all other variables are as originally defined.

Another aspect of the invention that is of particular interest relates to compounds of formula II wherein $Ar^4$ represents an aryl or heteroaryl group selected from the group consisting of benzene, pyridine, thiophene, furan, oxazole, thiazole, 1,3,4-thiadiazole and naphthalene, said group being optionally substituted with $R^3$. Within this subset, all other variables are as originally defined.

A preferred aspect of the invention relates to compounds represented by formula II wherein:

$Ar^1$ is an aryl or heteroaryl group substituted by $R^1$ and $R^3$;

$R^1$ is OH, $OCH_2Ar^3$, $SCH_2Ar^3$, $OAr^3$, $SAr^3$ or $NR^2CH_2Ar^3$;

$Ar^3$ is selected from the group consisting of benzene, pyridine, thiophene, furan, oxazole and thiazole, said group being optionally substituted with $R^3$;

$Ar^2$ represents a member selected from the group consisting of: benzene, pyridine, thiophene, furan, oxazole, and thiazole, said group being optionally substituted with 1–4 members selected from the group consisting of: $R^4$, $OR^4$, $SR^4$ and halogen;

W is selected from the group consisting of: $CH_2OCH_2$, $(CH_2)_3$, $CH_2CH$=CH, CH=$CHCH_2$, CH(OH)CH=CH, CH=CHCH(OH), $CH_2C$≡C , C≡$CCH_2$ 1,2-c-Pr—$CH_2$— and —$CH_2$-1,2-c-Pr-;

X is selected from the group consisting of: $(CH_2)_2$, CH=CH, C≡C and 1,2-c-Pr;

and Q is $CO_2H$ or tetrazole. Within this subset, all other variables are as originally defined.

Another preferred aspect of the invention relates to compounds represented by formula II wherein:

$Ar^1$ is an aryl or heteroaryl group optionally substituted with $R^1$ and $R^3$;

$R^1$ is OH, $OCH^2Ar^3$, $SCH_2Ar^3$, $OAr^3$, $SAr^3$ or $NR_2CH_2Ar^3$;

$Ar^3$ represents a member selected from the group consisting of: benzene, pyridine, thiophene, furan, oxazole or thiazole, said group being optionally substituted with $R^3$;

W is selected from the group consisting of: $CH_2OCH_2$, $(CH_2)_3$, $CH_2CH$=CH, CH=$CHCH_2$, CH(OH)CH=CH, CH=CHCH(OH), $CH_2C$+C or C≡$CCH_2$;

$Ar^2$ represents a member selected from the group consisting of: benzene, pyridine, thiophene, furan, oxazole or thiazole, said group being optionally substituted with $R^8$;

X is is selected from the group consisting of: $(CH_2)_2$, $CH=CH$, $C\equiv C$ and 1,2-c-Pr;

Q is $CONHSO_2ZAr^4$;

Z is a 0–2 carbon linker and is unsubstituted;

$Ar^4$ is selected from the group consisting of: benzene, pyridine, thiophene, furan, oxazole, thiazole, 1,3,4-thiadiazole and naphthalene, and is optionally substituted by $R^3$. Within this subset, all other variables are as originally defined.

A more preferred aspect of the invention relates to compounds represented by formula II wherein:

$Ar^1$ is benzene or thiophene substituted in position 2 and/or position 4 relative to the attachment of W with a member selected from the group consisting of: OH, $OCH_2Ar^3$, $SCH_2Ar^3$, $OAr^3$, $SAr^3$ and $NR^2CH_2Ar^3$, and is optionally substituted in position 3 with a member selected from the group consisting of: OMe, $OCHF_2$ and lower alkyl;

$Ar^3$ is benzene or thiophene, optionally substituted with $R^8$;

W is selected from the group consisting of: $CH_2OCH_2$, $(CH_2)_3$, $CH_2CH=CH$, $CH=CHCH_2$, $CH(OH)CH=CH$ and $CH=CHCH(OH)$, $Ar^2$ is benzene or thiophene, optionally substituted with 1–4 members selected from $R^4$, $OR^4$, $SR^4$ and halogen;

X represents a member selected from the group consisting of: $(CH_2)_2$, $CH=CH$ and 1,2-c-Pr, and Q is $CO_2H$.

Within this subset, all other variables are as originally defined.

Another more preferred aspect of the invention relates to compounds represented by formula II wherein:

$Ar^1$ is a benzene or a thiophene unsubstituted or substituted in position 2 and/or position 4 relative to the point of attachment to W by a member selected from the group consisting of: OH, $OCH_2Ar^3$, $SCH_2Ar^3$, $OAr^3$, $SAr^3$ and $NR^2CH_2Ar^3$; and is optionally substituted at position 3 with one member selected from the group consisting of: OMe, $OCHF_2$ and lower alkyl;

$Ar^3$ is benzene or thiophene, optionally substituted with $R^8$;

W is selected from the group consisting of: $CH_2OCH_2$, $(CH_2)_3$, $CH_2CH=CH$, $CH=CHCH_2$, $CH(OH)CH=CH$ and $CH=CHCH(OH)$;

$Ar^2$ is benzene or thiophene, optionally substituted with $R^4$, $OR^4$, $SR^4$ or halo;

X is selected from the group consisting of: $(CH_2)_2$, $CH=CH$ and 1,2-c-Pr,

Q is $CONHSO_2ZAr^4$,

Z is a bond or $CH^2$, and $Ar^4$ is selected from the group consisting of: benzene, thiophene, 1,3,4-thiadiazole and naphthalene and is substituted with $R^8$.

Within this subset, all other variables are as originally defined.

A particularly preferred aspect of the present invention that is of interest relates to compounds represented by formula II':

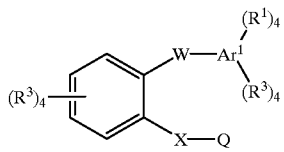

as well as pharmaceutically acceptable salts and hydrates thereof, wherein:

$Ar^1$ represents phenyl, naphthyl, benzofuranyl or methylenedioxyphenyl;

$R^1$ represents H, OH, $C_{1-6}$alkyl, $C_{1-6}$alkoxy, hydroxy$C_{1-6}$alkyl, aryl, aryloxy, arylalkoxy, haloaryl, haloheteroaryl, haloarylalkoxy, alkylaryl, haloalkylarylalkoxy, haloarylalkoxy and haloheteroarylalkoxy;

$R^3$ represents $R^4$, halogen, $OR^4$ or $SR^4$;

$R^4$ represents H, lower alkyl, lower alkenyl, lower alkynyl, $CHF_2$ or $CF_3$;

X represents a member selected from the group consisting of: $-(CH_2)_{1-2}-$, 1,2-c-Pr, $-CH=CH-$, $-CH_2O-$, $-C=CCH_2-$, $-C\equiv C-$, and $-CH_2-C\equiv C-$;

W represents a member selected from the group consisting of:

$-(CH_2)_{3-6}-$, $-CH_2CH=CH-$, $-CH=CHCH_2-$, $-CH(OH)CH=CH-$, $-CH=CHCH(OH)-$, $-CH_2-1,2-c-Pr-$, $-1,2-c-Pr-CH_2-$, $-CH_2-O-CH_2-$, $-O-(CH_2)_{1-3}-O-$, $-CH_2-NHC(O)-$, $-CF_2CH=CH-$, $-CH=CHCF_2-$, $-CH_2CH_2-S-$, $-S-CH_2CH_2-$, $-CH_2CH_2-SO_2-$, $-SO_2-CH_2CH_2-$, $-O-(CH_2)_{1-3}-$, $-(CH_2)_{1-3}-O-$ and $-CH=CHCH_2CH_2-$, and all other variables are as originally defined.

Another particularly preferred aspect of the invention relates to compounds represented by formula II":

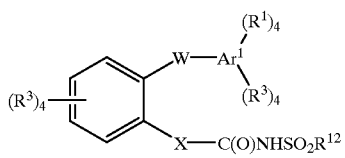

as well as pharmaceutically acceptable salts and hydrates thereof, wherein:

$Ar^1$ represents phenyl, naphthyl, benzofuranyl or methylenedioxyphenyl;

$R^1$ represents H, OH, $C_{1-6}$alkyl, $C_{1-6}$alkoxy, hydroxy$C_{1-6}$alkyl, aryl, aryloxy, arylalkoxy, haloaryl, haloheteroaryl, haloarylalkoxy, alkylaryl, haloalkylarylalkoxy, haloarylalkoxy and haloheteroarylalkoxy;

$R^3$ represents $R^4$, halogen, $OR^4$ or $SR^4$;

$R^4$ represents H, lower alkyl, lower alkenyl, lower alkynyl, $CHF_2$ or $CF_3$;

X represents a member selected from the group consisting of:

$-(CH_2)_{1-2}-$, $-1,2-c-Pr-$, $-CH=CH-$, $-CH_2O-$, $-C\equiv CCH_2-$, $-C\equiv C-$, and $-CH_2-C\equiv C-$;

W represents a member selected from the group consisting of:

$-(CH_2)_{3-6}-$, $-CH_2CH=CH-$, $-CH=CHCH_2-$, $-CH(OH)CH=CH-$,

—CH=CHCH(OH)—, —CH$_2$-1,2-c-Pr—, -1,2-c-Pr—CH$_2$—, —CH$_2$—O—CH$_2$—, —O—(CH$_2$)$_{1-3}$—O—, —CH$_2$—NHC(O)—, —CF$_2$CH=CH—, —CH=CHCF$_2$—, —CH$_2$CH$_2$—S—, —S—CH$_2$CH$_2$—, —CH$_2$CH$_2$—SO$_2$—, —SO$_2$—CH$_2$CH$_2$—, —O—(CH$_2$)$_{1-3}$—, —(CH$_2$)$_{1-3}$—O— and —CH=CHCH$_2$CH$_2$—, and R$^{12}$ is selected from the group consisting of: C$_{1-6}$alkyl, thienyl, phenyl, naphthyl, biphenyl, quinolinyl, thiadiazolyl, tetrazolyl, —CH=CH-phenyl, said thienyl, phenyl, naphthyl, biphenyl, quinolinyl, thiadiazolyl, tetrazolyl and —CH=CH-phenyl groups being optionally substituted with R$^3$.

Examples of compounds within the present application are the following:

TABLE I (Ar$^1$—W—Ar$^2$—X—Q)

| Ex | Ar$^1$ | W | Ar$^2$ | X | Q |
|---|---|---|---|---|---|
| 1 | 2-(BnO)-3-MePh | (CH$_2$)$_3$ | 1,2-Phe | (CH$_2$)$_2$ | CO$_2$H |
| 2 | 2-(BnO)-3-MePh | CH$_2$CH=CH | 1,2-Phe | CH=CH | CONHSO$_2$-2-thienyl |
| 3 | 2-(BnO)-3-MePh | CH=CHCH$_2$ | 1,2-Phe | CH=CH | CONHSO$_2$-2-thienyl |
| 4 | 2-((2-Cl-4-FPh)CH$_2$O)-3-CF$_3$Ph | CH$_2$CH=CH | 1,2-Phe | CH=CH | CO$_2$H |
| 5 | 2-((2-Cl-4-FPh)CH$_2$O)-3-CF$_3$Ph | CH=CHCH$_2$ | 1,2-Phe | CH=CH | CO$_2$H |
| 6 | 2-(BnO)Ph | CH$_2$CH=CH | 1,2-Phe | CH=CH | CO$_2$Na |
| 7 | 2-(BnO)Ph | CH=CHCH$_2$ | 1,2-Phe | CH=CH | CO$_2$Na |
| 8 | 4-(BnO)-3,5-(MeO)$_2$Ph | CH$_2$CH=CH | 1,2-Phe | CH=CH | CO$_2$Na |
| 9 | 4-(BnO)-3,5-(MeO)$_2$Ph | CH=CHCH$_2$ | 1,2-Phe | CH=CH | CO$_2$Na |
| 10 | 2-(BnO)-5-AcPh | CH$_2$CH=CH | 1,2-Phe | CH=CH | CO$_2$H |
| 11 | 2-(BnO)-5-AcPh | CH=CHCH$_2$ | 1,2-Phe | CH=CH | CO$_2$H |
| 12 | 2-(BnO)-3-(MeO)Ph | CH$_2$CH=CH | 1,2-Phe | CH=CH | CO$_2$Na |
| 13 | 2-(BnO)-3-(MeO)Ph | CH=CHCH$_2$ | 1,2-Phe | CH=CH | CO$_2$Na |
| 14 | 4-(BnO)-3-(MeO)Ph | CH$_2$CH=CH | 1,2-Phe | CH=CH | CO$_2$Na |
| 15 | 4-(BnO)-3-(MeO)Ph | CH=CHCH$_2$ | 1,2-Phe | CH=CH | CO$_2$Na |
| 16 | 2-(BnO O)-3-MePh | CH$_2$CH=CH | 1,2-Phe | CH$_2$ | CO$_2$Na |
| 17 | 2-(BnO)-3-MePh | CH=CHCH$_2$ | 1,2-Phe | CH$_2$ | CO$_2$Na |
| 18 | 2-(BnO)-3-MePh | CH$_2$CH=CH | 5-Cl-1,2-Phe | CH$_2$ | CO$_2$Na |
| 19 | 2-(BnO)-3-MePh | CH=CHCH$_2$ | 5-Cl-1,2-Phe | CH$_2$ | CO$_2$Na |
| 20 | 4-(BnO)-3-(MeO)Ph | (CH$_2$)$_3$ | 1,2-Phe | 1,2-c-Pr | CO$_2$H |
| 21 | 2-(BnO)-3-MePh | CH=CHCH$_2$ | 4,5-(MeO)$_2$-1,2-Phe | CH=CH | CO$_2$H |
| 22 | 2-(BnO)-3-MePh | CH$_2$CH=CH | 4,5-(MeO)$_2$-1,2-Phe | CH=CH | CO$_2$H |
| 23 | 3,4-(methylene dioxy)Ph | CH=CHCH$_2$ | 1,2-Phe | CH=CH | CO$_2$H |
| 24 | 3,4-(methylene dioxy)Ph | CH$_2$CH=CH | 1,2-Phe | CH=CH | CO$_2$H |
| 25 | Ph | CH=CHCH$_2$ | 1,2-Phe | CH=CH | CO$_2$H |
| 26 | Ph | CH$_2$CH=CH | 1,2-Phe | CH=CH | CO$_2$H |
| 27 | 2-(HO)-3-MePh | CH=CHCH$_2$ | 1,2-Phe | CH=CH | CO$_2$H |
| 28 | 2-(BnO)-3-MePh | CH=CHCH$_2$ | 1,2-Phe | CH=CH | CO$_2$Na |
| 29 | 2-(BnO)-3-MePh | CH$_2$CH=CH | 1,2-Phe | CH=CH | CO$_2$Na |
| 30 | 2-((7-Cl-2-quinolinyl)CH$_2$O)-3-MePh | CH=CHCH$_2$ | 1,2-Phe | CH=CH | CO$_2$H |
| 31 | 2-((7-Cl-2-quinolinyl)CH$_2$O)-3-Me Ph | CH$_2$CH=CH | 1,2-Phe | CH=CH | CO$_2$H |
| 32 | 2-(BnO)-3-MePh | (CH$_2$)$_3$ | 1,2-Phe | bond | CO$_2$H |
| 33 | 2-(BnO)-3- | CH=CHCH$_2$ | 1,2-Phe | bond | CO$_2$Na |

TABLE I-continued (Ar$^1$—W—Ar$^2$—X—Q)

| Ex | Ar$^1$ | W | Ar$^2$ | X | Q |
|---|---|---|---|---|---|
| 34 | 2-(BnO)-3-MePh | CH$_2$CH=CH | 1,2-Phe | bond | CO$_2$Na |
| 35 | 2-(BnO)-3-MePh | (CH$_2$)$_3$ | 1,2-Phe | CH=CH | CO$_2$Na |
| 36 | 2-(BnO)-3-(MeO)Ph | (CH$_2$)$_3$ | 1,2-Phe | CH=CH | CO$_2$Na |
| 37 | 4-(BnO)-3-(MeO)Ph | (CH$_2$)$_3$ | 1,2-Phe | CH=CH | CO$_2$Na |
| 38 | 4-(MeO)Ph | CH$_2$CH=CH | 1,2-Phe | CH=CH | CO$_2$H |
| 39 | 4-(MeO)Ph | CH=CHCH$_2$ | 1,2-Phe | CH=CH | CO$_2$H |
| 40 | 3,4-(MeO)$_2$Ph | CH$_2$CH=CH | 1,2-Phe | CH=CH | CO$_2$H |
| 41 | 3,4-(MeO)$_2$Ph | CH=CHCH$_2$ | 1,2-Phe | CH=CH | CO$_2$H |
| 42 | 2-(BnO)Ph | CH(OH)CH=CH | 1,2-Phe | CH=CH | CO$_2$Na |
| 43 | 2-(BnO)-3-MePh | (CH$_2$)$_3$ | 1,2-Phe | (CH$_2$)$_2$ | CONNaSO$_2$-2-thienyl |
| 44 | 4-(BnO)-3-(MeO)Ph | CH$_2$CH=CH | 1,2-Phe | CH=CH | CONNaSO$_2$-2-thienyl |
| 45 | 4-(BnO)-3-(MeO)Ph | CH=CHCH$_2$ | 1,2-Phe | CH=CH | CONNaSO$_2$-2-thienyl |
| 46 | 2-(BnO)-3-MePh | CH$_2$-1,2-c-Pr | 1,2-Phe | CH=CH | CO$_2$Na |
| 47 | 2-(BnO)-3-MePh | 1,2-c-Pr-CH$_2$ | 1,2-Phe | CH=CH | CO$_2$Na |
| 48 | 2-(BnO)-3-MePh | CH(OH)CH=CH | 1,2-Phe | CH=CH | CO$_2$Na |
| 49 | 2-(BnO)-3 MePh | CH=CHCH(OH) | 1,2-Phe | CH=CH | CO$_2$H |
| 50 | 2-((2,6-Cl$_2$Ph)CH$_2$O)-3-MePh | CH=CHCH(OH) | 1,2-Phe | CH=CH | CO$_2$H |
| 51 | 2-((2,6-Cl$_2$Ph)CH$_2$O)-3-MePh | CH(OH)CH=CH | 1,2-Phe | CH=CH | CO$_2$H |
| 52 | 2-((4-FPh)CH$_2$O)-3-MePh | CH$_2$CH=CH | 1,2-Phe | CH=CH | CO$_2$H |
| 53 | 2-((4-FPh)CH$_2$O)-3-MePh | CH=CHCH$_2$ | 1,2-Phe | CH=CH | CO$_2$Na |
| 54 | 2-((3,4-F$_2$Ph)CH$_2$O)-3-MePh | CH$_2$CH=CH | 1,2-Phe | CH=CH | CO$_2$H |
| 55 | 2-((3,4-F$_2$Ph)CH$_2$O)-3-MePh | CH=CHCH$_2$ | 1,2-Phe | CH=CH | CO$_2$Na |
| 56 | 2-((3,5-F$_2$Ph)CH$_2$O)-3-MePh | CH$_2$CH=CH | 1,2-Phe | CH=CH | CO$_2$H |
| 57 | 2-((3,5-F$_2$Ph)CH$_2$O)-3-MePh | CH=CHCH$_2$ | 1,2-Phe | CH=CH | CO$_2$Na |
| 58 | 2-((2,6-Cl$_2$Ph)CH$_2$O)-3-(HOCH$_2$)Ph | CH$_2$CH=CH | 1,2-Phe | CH=CH | CO$_2$H |
| 59 | 2-((2,6-Cl$_2$Ph)CH$_2$O)-3-(HOCH$_2$)Ph | CH=CHCH$_2$ | 1,2-Phe | CH=CH | CO$_2$H |
| 60 | 2-((2,6-Cl$_2$Ph)CH$_2$O)-3-MePh | CH$_2$CH=CH | 1,2-Phe | CH=CH | CO$_2$H |
| 61 | 2-((2,6-Cl$_2$Ph)CH$_2$O)-3-MePh | CH=CHCH$_2$ | 1,2-Phe | CH=CH | CO$_2$Na |
| 62 | 2-((4-CF$_3$Ph)CH$_2$O)-3-MePh | CH$_2$CH=CH | 1,2-Phe | CH=CH | CO$_2$H |
| 63 | 2-((4-CF$_3$Ph)CH$_2$O)-3-MePh | CH=CHCH$_2$ | 1,2-Phe | CH=CH | CO$_2$Na |
| 64 | 2-((4-(CHF$_2$O)Ph)CH$_2$O)-3-MePh | CH$_2$CH=CH | 1,2-Phe | CH=CH | CO$_2$H |
| 65 | 2-((4-(CHF$_2$O)Ph)CH$_2$O)-3-MePh | CH=CHCH$_2$ | 1,2-Phe | CH=CH | CO$_2$Na |
| 66 | 2-((4-CF$_3$Ph)CH$_2$O)-3-(HOCH$_2$)Ph | CH=CHCH(OH) | 1,2-Phe | CH=CH | CO$_2$H |
| 67 | 2-((4-CF$_3$Ph)CH$_2$O)-3-(HOCH$_2$)Ph | CH=CHCH$_2$ | 1,2-Phe | CH=CH | CO$_2$H |
| 68 | 2-((4-CF$_3$Ph)CH$_2$O)-3-MePh | CH=CHCH(OH) | 1,2-Phe | CH=CH | CO$_2$H |
| 69 | 2-(PhCH$_2$O)-3-(HOCH$_2$)Ph | CH=CHCH$_2$ | 1,2-Phe | CH=CH | CO$_2$H |
| 70 | 3-(PhO)Ph | CH$_2$OCH$_2$ | 1,2-Phe | CH=CH | CO$_2$Na |

TABLE I-continued (Ar$^1$—W—Ar$^2$—X—Q)

| Ex | Ar$^1$ | W | Ar$^2$ | X | Q |
|---|---|---|---|---|---|
| 71 | 2-(PhO)Ph | CH$_2$OCH$_2$ | 1,2-Phe | CH=CH | CO$_2$Na |
| 72 | 3-(BnO)Ph | CH$_2$CH=CH | 1,2-Phe | CH=CH | CO$_2$Na |
| 73 | 3-(BnO)Ph | CH=CHCH$_2$ | 1,2-Phe | CH=CH | CO$_2$Na |
| 74 | 2-(BnO)Ph | O(CH$_2$)$_3$O | 1,2-Phe | CH=CH | CO$_2$Na |
| 75 | 2-(PhCHMeO)-3-MePh | CH=CHCH$_2$ | 1,2-Phe | CH=CH | CO$_2$Na |
| 76 | 2-(PhCHMeO)-3-MePh | CH$_2$CH=CH | 1,2-Phe | CH=CH | CO$_2$H |
| 77 | 3-(PhO)Ph | CH=CHCH$_2$ | 1,2-Phe | CH=CH | CO$_2$Na |
| 78 | 3-(PhO)Ph | CH$_2$CH=CH | 1,2-Phe | CH=CH | CO$_2$Na |
| 79 | 3-Ph benzofuran-7-yl | CH=CHCH$_2$ | 1,2-Phe | CH=CH | CO$_2$Na |
| 80 | 3-Ph benzofuran-7-yl | CH$_2$CH=CH | 1,2-Phe | CH=CH | CO$_2$Na |
| 81 | Ph | CH=CHCH$_2$ | 1,2-Phe | CH=CH | CONHSO$_2$-2-thienyl |
| 82 | Ph | CH$_2$CH=CH | 1,2-Phe | CH=CH | CONHSO$_2$-2-thienyl |
| 83 | 4-(MeO)Ph | CH=CHCH$_2$ | 1,2-Phe | CH=CH | CONHSO$_2$-2-thienyl |
| 84 | 4-(MeO)Ph | CH$_2$CH=CH | 1,2-Phe | CH=CH | CONHSO$_2$-2-thienyl |
| 85 | 2-(BnO)-1-naphthyl | CH$_2$NHCO | 1,2-Phe | CH=CH | CO$_2$H |
| 86 | 2-((2-Cl-4-FPh)CH$_2$O)-3-MePh | CH$_2$CH=CH | 1,2-Phe | CH=CH | CO$_2$H |
| 87 | 2-((2-Cl-4-FPh)CH$_2$O)-3-MePh | CH=CHCH$_2$ | 1,2-Phe | CH=CH | CO$_2$H |
| 88 | 2-((2,4-F$_2$Ph)CH$_2$O)-3-MePh | CH$_2$CH=CH | 1,2-Phe | CH=CH | CO$_2$H |
| 89 | 2-((2,4-F$_2$Ph)CH$_2$O)-3-MePh | CH=CHCH$_2$ | 1,2-Phe | CH=CH | CO$_2$H |
| 90 | 2-((2,4,6-F$_3$Ph)CH$_2$O)-3-MePh | CH$_2$CH=CH | 1,2-Phe | CH=CH | CO$_2$H |
| 91 | 2-((2,4,6-F$_3$Ph)CH$_2$O)-3-MePh | CH=CHCH$_2$ | 1,2-Phe | CH=CH | CO$_2$H |
| 92 | 2-((2,6-Cl$_2$-4-FPh)CH$_2$O)-3-MePh | CH$_2$CH=CH | 1,2-Phe | CH=CH | CO$_2$H |
| 93 | 2-((2,6-Cl$_2$-4-FPh)CH$_2$O)-3-MePh | CH=CHCH$_2$ | 1,2-Phe | CH=CH | CO$_2$H |
| 94 | 2-((2,4-F$_2$Ph) CH$_2$O)-3-(CHF$_2$O)Ph | CH$_2$CH=CH | 1,2-Phe | CH=CH | CO$_2$H |
| 95 | 2-((2,4-F$_2$Ph) CH$_2$O)-3-(CHF$_2$O)Ph | CH=CHCH$_2$ | 1,2-Phe | CH=CH | CO$_2$H |
| 96 | 2-((4-FPh)CH$_2$O)-3-MePh | CF$_2$CH=CH | 1,2-Phe | CH=CH | CO$_2$H |
| 97 | 2-((4-FPh)CH$_2$O)-3-MePh | CH=CHCF$_2$ | 1,2-Phe | CH=CH | CO$_2$H |
| 98 | 2-((4-FPh)CH$_2$O)-3-MePh | (CH$_2$)$_3$ | 1,2-Phe | CH=CH | CONHSO$_2$-(4-i-PrPh) |
| 99 | 2-((4-FPh)CH$_2$O)-3-MePh | (CH$_2$)$_3$ | 1,2-Phe | CH=CH | CONHSO$_2$-(4-t-BuPh) |
| 100 | 2-((4-FPh)CH$_2$O)-3-MePh | CH$_2$CH=CH | 1,2-Phe | CH=CH | CONHSO$_2$-(4-(MeO)Ph) |
| 101 | 2-((4-FPh)CH$_2$O)-3-MePh | CH=CHCH$_2$ | 1,2-Phe | CH=CH | CONHSO$_2$-(2,3-Cl$_2$Ph) |
| 102 | 2-((4-FPh)CH$_2$O)-3-MePh | CH=CHCH$_2$ | 4-Cl-1,2-Phe | CH=CH | CONHSO$_2$-(5-Br-2-(MeO)Ph) |
| 103 | 2-((4-FPh)CH$_2$O)-3-MePh | (CH$_2$)$_2$S | 3-F-1,2-Phe | CH=CH | CONHSO$_2$-(2,3,4-Cl$_3$Ph) |
| 104 | 2-((4-FPh)CH$_2$O)-3-MePh | (CH$_2$)$_2$S | 6-CF$_3$-1,2-Phe | CH=CH | CONHSO$_2$-(5-F-2-MePh) |
| 105 | 2-((4-FPh) | (CH$_2$)$_2$S | 4,5-F$_2$-1,2- | CH=CH | CONHSO$_2$- |

TABLE I-continued (Ar¹—W—Ar²—X—Q)

| Ex | Ar¹ | W | Ar² | X | Q |
|---|---|---|---|---|---|
| 106 | 2-((4-FPh)CH$_2$O)-3-MePh | (CH$_2$)$_2$SO$_2$ | Ph 1,2-Phe | CH=CH | (2,5-Me$_2$Ph) CONHSO$_2$-(4-CF$_3$Ph) |
| 107 | 2-((4-FPh)CH$_2$O)-3-MePh | (CH$_2$)$_2$SO$_2$ | 1,2-Phe | CH=CH | CONHSO$_2$-2-naphthyl |
| 108 | 2-((4-FPh)CH$_2$O)-3-MePh | CH=CHCH$_2$ | 3-F-1,2-Phe | CH=CH | CONHSO$_2$-(3-Cl-4-FPh) |
| 109 | 2-((4-FPh)CH$_2$O)-3-MePh | SO$_2$(CH$_2$)$_2$ | 1,2-Phe | CH=CH | CONHSO$_2$-(4-n-PrPh) |
| 110 | 2-((4-FPh)CH$_2$O)-3-(MeO)Ph | SO$_2$(CH$_2$)$_2$ | 1,2-Phe | CH=CH | CONHSO$_2$-(2-ClPh) |
| 111 | 2-((4-FPh)CH$_2$O)-3-(MeO)Ph | SO$_2$(CH$_2$)$_2$ | 1,2-Phe | CH=CH | CONHSO$_2$-(4-FPh) |
| 112 | 2-((4-FPh)CH$_2$O)-3-(MeO)Ph | S(CH$_2$)$_2$ | 1,2-Phe | CH=CH | CONHSO$_2$-(2-PhPh) |
| 113 | 2-((4-FPh)CH$_2$O)-3-(MeO)Ph | S(CH$_2$)$_2$ | 1,2-Phe | CH=CH | CONHSO$_2$-(2-CF$_3$Ph) |
| 114 | 2-((4-FPh)CH$_2$O)-3-(MeO)Ph | S(CH$_2$)$_2$ | 4-t-Bu-1,2-Phe | CH=CH | CONHSO$_2$-(4-Cl-2,5-Me$_2$Ph) |
| 115 | 2-((4-FPh)CH$_2$O)-3-(MeO)Ph | O(CH$_2$)$_2$ | 1,2-Phe | CH=CH | CONHSO$_2$-(2,5-Cl$_2$Ph) |
| 116 | 2-((4-FPh)CH$_2$O)-3-(MeO)Ph | O(CH$_2$)$_2$ | 1,2-Phe | CH=CH | CONHSO$_2$-(4-Br-2-(CF$_3$O)Ph) |
| 117 | 2-((4-FPh)CH$_2$O)-3-(MeO)Ph | O(CH$_2$)$_2$ | 1,2-Phe | CH=CH | CONHSO$_2$-CH$_2$Ph |
| 118 | 2-((4-FPh)CH$_2$O)-3-(MeO)Ph | (CH$_2$)$_2$O | 1,2-Phe | CH=CH | CONHSO$_2$-1-naphthyl |
| 119 | 2-((4-FPh)CH$_2$O)-3-(MeO)Ph | (CH$_2$)$_2$O | 4,5-F$_2$-1,2-Phe | CH=CH | CONHSO$_2$-(2-FPh) |
| 120 | 2-((4-FPh)CH$_2$O)-3-(MeO)Ph | (CH$_2$)$_2$O | 1,2-Phe | CH=CH | CONHSO$_2$-(2,4-Cl$_2$Ph) |
| 121 | 2-((4-FPh)CH$_2$O)-3-(MeO)Ph | (CH$_2$)$_3$ | 1,2-Phe | CH=CH | CONHSO$_2$-CH=CHPh |
| 122 | 2-((4-FPh)CH$_2$O)-3-(MeO)Ph | (CH$_2$)$_3$ | 1,2-Phe | CH=CH | CONHSO$_2$-(3,5-(CF$_3$)$_2$Ph) |
| 123 | 2-((4-FPh)CH$_2$O)Ph | (CH$_2$)$_3$ | 1,2-Phe | CH=CH | CONHSO$_2$-(2,5-Cl$_2$-3-thienyl) |
| 124 | 2-((4-FPh)CH$_2$O)Ph | (CH$_2$)$_4$ | 3-F-1,2-Phe | CH=CH | CONHSO$_2$-(3-BrPh) |
| 125 | 2-((4-FPh)CH$_2$O)Ph | (CH$_2$)$_4$ | 3-MeO-1,2-Phe | CH=CH | CONHSO$_2$-(2-BrPh) |
| 126 | 2-((4-FPh)CH$_2$O)Ph | (CH$_2$)$_4$ | 1,2-Phe | CH=CH | CONHSO$_2$-(2-NO$_2$Ph) |
| 127 | 2-((4-FPh)CH$_2$O)Ph | (CH$_2$)$_5$ | 1,2-Phe | (CH$_2$)$_2$ | CONHSO$_2$-(3-ClPh) |
| 128 | 2-((4-FPh)CH$_2$O)Ph | (CH$_2$)5 | 1,2-Phe | (CH$_2$)$_2$ | CONHSO$_2$-(4-(CF$_3$O)Ph) |
| 129 | 2-HOPh | CH=CH(CH$_2$)$_2$ | 1,2-Phe | (CH$_2$)$_2$ | CONHSO$_2$-8-quinolinyl |
| 130 | 2-((4-FPh)CH$_2$O)Ph | CH=CH(CH$_2$)$_2$ | 5-(CF$_3$O)-1,2-Phe | (CH$_2$)$_2$ | CONHSO$_2$-(3,4-Cl$_2$Ph) |
| 131 | 4-((2,6-Cl$_2$-4-FPh)CH$_2$O)-3-MePh | CH=CH(CH$_2$)$_2$ | 3-F-1,2-Phe | (CH$_2$)$_2$ | CONHSO$_2$-(4-EtPh) |
| 132 | 2-((4-FPh)CH$_2$O)Ph | CH$_2$CH=CH | 1,2-Phe | (CH$_2$)$_2$ | CONHSO$_2$-(4-Cl-2-NO$_2$Ph) |
| 133 | 2-((4-FPh)CH$_2$O)Ph | CH=CHCH$_2$ | 4,5-F$_2$-1,2-Phe | CH=CH | CONHSO$_2$-(2-Cl-3-Br-5-thienyl) |
| 134 | 2-((4-FPh)CH$_2$O)Ph | CH$_2$CH=CH | 4,5-F$_2$-1,2-Phe | CH=CH | CONHSO$_2$-(3,4- |

TABLE I-continued (Ar¹—W—Ar²—X—Q)

| Ex | Ar¹ | W | Ar² | X | Q |
|---|---|---|---|---|---|
| 135 | 2-HOPh | CH=CHCH$_2$ | 4,5-F$_2$-1,2-Phe | CH=CH | CONHSO$_2$-(2,5-Cl$_2$-3-Br-4-thienyl) |
| 136 | 4-((4-FPh)CH$_2$O)-3-(MeO)Ph | CH$_2$CH=CH | 4,5-F$_2$-1,2-Phe | CH=CH | CONHSO$_2$-(4-Br-2,5-F$_2$Ph) |
| 137 | 4-((4-FPh)CH$_2$O)-3-(MeO)Ph | CH=CHCH$_2$ | 1,2-Phe | CH=CH | CONHSO$_2$-(5-(AcNH)-1,3,4-thiadiazol-2-yl) |
| 138 | 4-((4-FPh)CH$_2$O)-3-(MeO)Ph | CH$_2$CH=CH | 1,2-Phe | CH=CH | CONHSO$_2$-(2,3,4,5,6-F$_5$Ph) |
| 139 | 4-((2-Cl-4-FPh)CH$_2$O)-3-MePh | CH=CHCH$_2$ | 1,2-Phe | CH=CH | CONHSO$_2$-(2-CNPh) |
| 140 | 2-((4-FPh)CH$_2$O)Ph | CH$_2$CH=CH | 4-F-1,2-Phe | CH=CH | CONHSO$_2$-(2-Cl-6-MePh) |
| 141 | 2-HOPh | CH=CHCH$_2$ | 1,2-Phe | CH=CH | CONHSO$_2$-(2,4,6-Me$_3$Ph) |
| 142 | Ph | CH$_2$CH=CH | 1,2-Phe | CH=CH | CONHSO$_2$-(2,3-Br$_2$-2-thienyl) |
| 143 | 2-((4-FPh)CH$_2$O)Ph | CH=CHCH$_2$ | 1,2-Phe | CH$_2$O | CONHSO$_2$-(4-NO$_2$Ph) |
| 144 | 2-((4-FPh)CH$_2$O)Ph | CH$_2$CH=CH | 1,2-Phe | CH$_2$O | CONHSO$_2$-(3,5-Cl$_2$Ph) |
| 145 | 2,4-((4-FPh)CH$_2$O)$_2$Ph | CH=CHCH$_2$ | 1,2-Phe | prop-1-yne-1,3-diyl | CONHSO$_2$-(5 Cl-2-thienyl) |
| 146 | 4-((2,4-F$_2$Ph)CH$_2$O)-3-(MeO)Ph | CH$_2$CH=CH | 1,2-Phe | CH$_2$O | CONHSO$_2$-(4-CF$_3$Ph) |
| 147 | 2-HO-3-MePh | CH=CHCH$_2$ | 1,2-Phe | CH$_2$O | CONHSO$_2$-(2,4-F$_2$Ph) |
| 148 | 2-((4-FPh)CH$_2$O)Ph | CH$_2$CH=CH | 4-F-1,2-Phe | 1,2-ethynediyl | CONHSO$_2$-(4-ClPh) |
| 149 | 2-((4-FPh)CH$_2$O)Ph | CH=CHCH$_2$ | 1,2-Phe | 1,2-ethynediyl | CONHSO$_2$-(3-CF$_3$Ph) |
| 150 | 4-HOPh | CH$_2$CH=CH | 1,2-Phe | 1,2-ethynediyl | CONHSO$_2$-Ph |
| 151 | 2-((4-FPh)CH$_2$O)Ph | CH=CHCH$_2$ | 1,2-Phe | prop-2-yne-1,3-diyl | CONHSO$_2$-(5-Br-2-thienyl) |
| 152 | 2,4-((4-FPh)CH$_2$O)$_2$Ph | CH$_2$CH=CH | 1,2-Phe | 1,2-ethynediyl | CONHSO$_2$-Me |
| 153 | 2,4-((4-FPh)CH$_2$O)$_2$Ph | CH=CHCH$_2$ | 1,2-Phe | 1,2-c-Pr | CONHSO$_2$-(2,5-(MeO)$_2$Ph) |
| 154 | 6-((4-FPh)CH$_2$O)-2-naphthyl | CH$_2$CH=CH | 4-F-1,2-Phe | 1,2-c-Pr | CONHSO$_2$-(3-MePh) |
| 155 | 2-((4-FPh)CH$_2$O)Ph | CH=CHCH$_2$ | 1,2-Phe | 1,2-c-Pr | CONHSO$_2$-(4-MePh) |
| 156 | 4-HO-3-(MeO)Ph | CH$_2$CH=CH | 1,2-Phe | 1,2-c-Pr | CONHSO$_2$-n-Bu |
| 157 | 4-((4-FPh)CH$_2$O)-1-naphthyl | CH=CHCH$_2$ | 1,2-Phe | 1,2-c-Bu | CONHSO$_2$-(2-Cl-4-FPh) |
| 158 | Ph | CH$_2$CH=CH | 1,2-Phe | CH=CH | CONHSO$_2$-(2-MePh) |
| 159 | 2-((4-FPh)CH$_2$O)Ph | CH=CHCH$_2$ | 1,2-Phe | CH=CH | CONHSO$_2$-c-Pr |
| 160 | 2,4-((4-FPh)CH$_2$O)$_2$Ph | CH=CHCH$_2$ | 1,2-Phe | CH=CH | CO$_2$H |
| 161 | 4-((2,4-F$_2$Ph)CH$_2$O)-3-(MeO)Ph | (CH$_2$)$_3$ | 4-F-1,2-Phe | CH=CH | 1H-tetrazol-5-yl |
| 162 | 2-((4-FPh)CH$_2$O)Ph | CH=CHCH$_2$ | 3-MeO-1,2-Phe | CH=CH | 1H-tetrazol-5-yl |
| 163 | 2,4-((4-FPh)CH$_2$O)$_2$Ph | CH=CHCH$_2$ | 1,2-Phe | CH=CH | 1H-tetrazol-5-yl |
| 164 | 4-HO-3-(MeO)Ph | CH=CHCH$_2$ | 1,2-Phe | 1,2-c-Pr | 1H-tetrazol-5-yl |
| 165 | Ph | CH=CHCH$_2$ | 1,2-Phe | (CH$_2$)$_2$ | 1H-tetrazol-5-yl |
| 166 | 2-((4-FPh)CH$_2$O)- | CH=CHCH$_2$ | 1,2-Phe | CH=CH | SO$_3$H |

TABLE I-continued

| | | (Ar¹—W—Ar²—X—Q) | | | |
|---|---|---|---|---|---|
| Ex | Ar¹ | W | Ar² | X | Q |
| 167 | 3-(Me O)Ph 2-((4-FPh)CH$_2$O)-3-MePh | (CH$_2$)$_3$ | 4-F-1,2-Phe | (CH$_2$)$_2$ | SO$_3$H |

Optical Isomers—Diastereomers—Geometric Isomers

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

Salts

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic, manganous, potassium, sodium, zinc salts, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that in the discussion of methods of treatment which follows, references to the compounds of Formula II are meant to also include the pharmaceutically acceptable salts and hydrates.

Dose Ranges

The magnitude of a prophylactic or therapeutic dose of a compound of Formula II will, of course; vary with the nature and the severity of the condition to be treated and with the particular compound of Formula II and its route of administration. It will also vary according to a variety of factors including the age, weight, general health, sex, diet, time of administration, rate of excretion, drug combination and response of the individual patient. In general, the daily dose from about 0.001 mg to about 100 mg per kg body weight of a mammal, preferably 0.01 mg to about 10 mg per kg. On the other hand, it may be necessary to use dosages outside these limits in some cases.

The active ingredient that may be combined with the carrier materials to produce a single dosage form will vary depending upon the host treated and the particular mode of administration. For example, a formulation intended for oral administration to humans may contain from as low as about 0.5 mg to as high as about 5 g of active agent, compounded with an appropriate and convenient amount of carrier material which may vary from about 5 to about 95 percent of the total composition. Dosage units will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical Compositions

The pharmaceutical compositions of the present invention comprise a compound of Formula II as an active ingredient or a pharmaceutically acceptable salt or hydrate, thereof, and may also contain a pharmaceutically acceptable carrier and optionally other therapeutic ingredients.

For the treatment of any of the prostanoid mediated diseases compound II may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compound II may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing the compound of Formula II are employed. (For purposes of this application, topical application shall include mouth washes and gargles.) Topical formulations may generally be comprised of a pharmaceutical carrier, cosolvent, emulsifier, penetration enhancer, preservative system, and emollient.

The composition of the present invention may also include additional therapeutic agents. For example, conventional analgesics such as aspirin or acetaminophen may be incorporated into the composition. Other examples of additional therapeutic agents which can be included are NSAIDs, such as ibuprofen or naproxen, COX-2 selective compounds, such as those which are described in the following patents and published applications: WO96/25405, U.S. Pat. No. 5,633,272, WO97/38986, U.S. Pat. No. 5,466, 823, WO98/03484, WO97/14691 and WO95/00501, and other compounds.

Utilities

The ability of the compounds of Formula II to interact with prostaglandin receptors makes them useful for preventing or reversing undesirable symptoms caused by prostaglandins in a mammalian, especially human, subject. This mimicking or antagonism of the actions of prostaglandins indicates that the compounds and pharmaceutical compositions thereof are useful to treat, prevent, or ameliorate in mammals and especially in humans: Pain, fever and inflammation of a variety of conditions including rheumatic fever, symptoms associated with influenza or other viral infections, common cold, low back and neck pain, skeletal pain, post-partum pain, dysmenorrhea, headache, migraine, toothache, sprains and strains, myositis, neuralgia, synovitis, arthritis, including rheumatoid arthritis, degenerative joint diseases (osteoarthritis), gout and ankylosing spondylitis, bursitis, burns including radiation and corrosive chemical injuries, sunburns, pain following surgical and dental procedures as well as immune and autoimmune diseases. In addition, such a compound may inhibit cellular neoplastic transformations and metastatic tumor growth and hence can be used in the treatment of cancer. Compounds of formula II is also of use in the treatment and/or prevention prostaglandin-mediated proliferation disorders such as may occur in diabetic retinopathy and tumor angiogenesis.

Compounds of formula II inhibit prostanoid-induced smooth muscle contraction by antagonizing contractile prostanoids or mimicking relaxing prostanoids and hence may be use in the treatment of dysmenorrhea, premature labor, asthma and eosinophil related disorders. It will also be of use in the treatment of Alzheimer's disease, the treatment of glaucoma, for the prevention of bone loss (treatment of osteoporosis) and for the promotion of bone formation (treatment of fractures) and other bone diseases such as Paget's disease.

By virtue of its prostanoid or prostanoid antagonist activity, compound II are useful as an alternative to conventional non-steroidal anti-inflammatory drugs (NSAID'S) particularly where such non-steroidal anti-inflammatory drugs may be contraindicated such as in patients with peptic ulcers, gastritis, regional enteritis, ulcerative colitis, diverticulitis or with a recurrent history of gastrointestinal lesions; GI bleeding, coagulation disorders including anemia such as hypoprothrombinemia, haemophilia or other bleeding problems; kidney disease; thrombosis, occlusive vascular diseases; those prior to surgery or taking anti-coagulants. Compound II will also be useful as a cytoprotective agent for patients undergoing chemotherapy.

Consequently one aspect of the invention addresses a method of treating or preventing a prostaglandin mediated disease in a mammalian patient in need thereof, comprising admininstering to said patient a compound in accordance withformula II in an amount which is effective for treating or preventing said prostaglandin mediated disease.

In another aspect of the invention, a method of treating or preventing a prostaglandin mediated disease is described which is further comprised of administering to said patient an effective amount of a COX-2 selective inhibiting compound.

More particularly, a method of treating or preventing a prostaglandin mediated disease is addressed wherein the prostaglandin mediated disease is selected from the group consisting of:

pain, fever, inflammation, rheumatic fever, symptoms associated with influenza or other viral infections, common cold, low back and neck pain, skeletal pain, postpartum pain, dysmenorrhea, headache, migraine, toothache, sprains, strains, myositis, neuralgia, synovitis, arthritis including rheumatoid arthritis, degenerative joint diseases (osteoarthritis), gout, ankylosing spondylitis, bursitis, burns including radiation and corrosive chemical injuries, sunburns, pain following surgical and dental procedures, immune and autoimmune diseases, cellular neoplastic transformations, metastatic tumor growth, prostaglandin-mediated proliferation disorders such as diabetic retinopathy and tumor angiogenesis, dysmenorrhea, premature labor, asthma, eosinophil related disorders, Alzheimer's disease, glaucoma, bone loss (osteoporosis), promotion of bone formation (treatment of fractures) and other bone diseases such as Paget's disease.

Further, a method of treating or preventing an E type prostaglandin mediated disease in a mammalian patient is described herein, comprising administering to said patient an amount of an E type prostaglandin ligand in an amount which is effective to treat or prevent said E type prostaglandin mediated disease.

More particularly, the method described with respect to E-typ prostaglandin mediated diseases further comprises administering a COX-2 selective inhibitor.

Examples of COX-2 selective compounds are such as those described in the following patents and published applications: WO96/25405, U.S. Pat. No. 5,633,272, WO97/38986, U.S. Pat. No. 5,466,823, WO98/03484, WO97/14691 and WO95/00501.

Methods of Synthesis

Compounds of the present invention can be prepared according to the following methods. Methods A, I and J showed how to form the linker W between $Ar^1$ and $Ar^2$; methods B and E–H concentrate on linker X; method C explained how to obtain sulfonamides and method D illustrate how to substitute Ar1. One particular method is usually used in conjunction with other methods to yield compounds of formula II. Reagents given below are for illustration of the chemistry only and should not be limiting this patent: other reagents might be as effective or better for each reaction described.

Method A

An aryl alkene I can be coupled with an aryl bromide, iodide or triflate II in the presence of a catalyst such as $Pd(OAc)_2$ to give the two isomers III and IV. Catalytic hydrogenation of the. double bond, using Pd/C or $(Ph_3P)_3RhCl$, yield the compound VI. Alternatively, VI can be prepared from I via formation of the boronate V with 9-borabicyclo[3.3.1]nonane and coupling with II in the presence of a catalyst such as $PdCl_2(dppf)$. Cyclopropanation of the alkenes III and IV can be performed using conditions such as $CH_2N_2/PdOAc_2$ to give VII and VIII. The group X-Q in compounds III, IV, VI, VII and VIII can then be transformed to another X-Q group to afford other substructures of II.

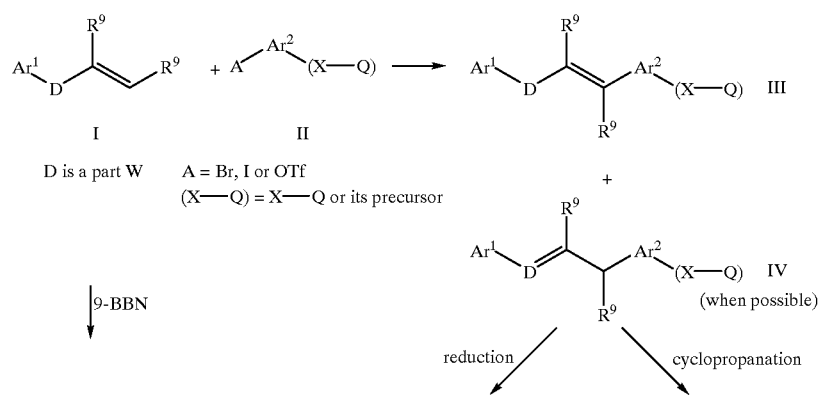

-continued

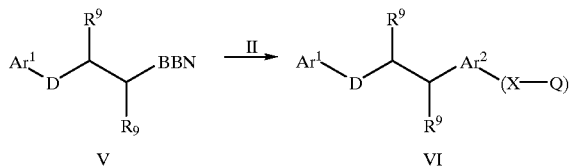

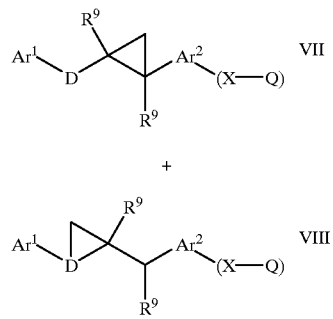

Method B

The acid or esters IX can be reduced to the alcohol X using reagents such as diisobutylaluminum hydride or sodium borohydride. Oxidation to the aldehyde XI can be performed using $MnO_2$ or pyridinium chlorochromate. Wittig reaction on XI afford the propenoate XII which can be cyclopropanated ($CH_2N_2$/Pd(OAc)$_2$) to XIII or reduced ($H_2$/Pd/C) to XIV. When R=H, compounds IX, XII, XIII and XIV are substructures of II.

coupling reagent such as 1-(3-dimethylaminopropyl)-3-ethylcarbodiimide. Another method for the preparation of XVI involves the formation of an acid chloride or a mixed anhydride XVII and reaction with the sulfonamine in the presence of a base such as $Et_3N$.

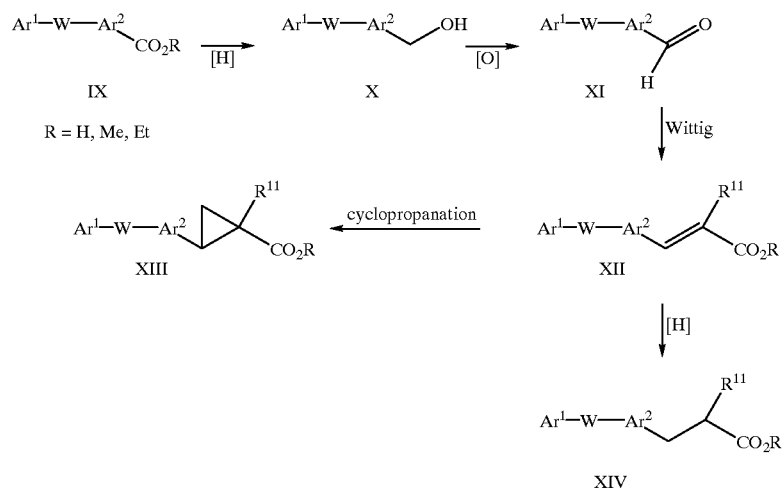

Method C

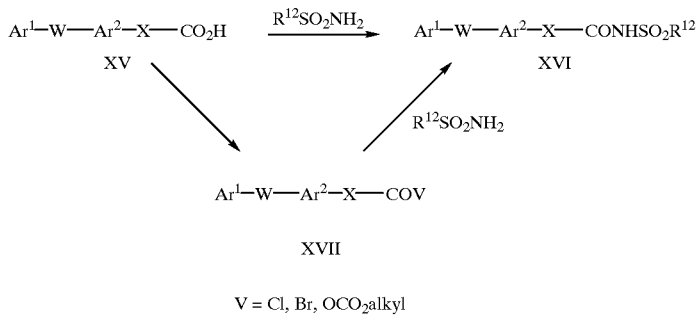

The acid XV, which is a substructure of II, can be transformed to the sulfonamide XVI, another substructure of II, by treatment with a sulfonamine in the presence of a Method D When compound II or its precursor is substituted by an hydroxyl group as in XVIII, it can be alkylated by a reagent containing a leaving group XIX in the presence of a base such as NaH or DBU to yield the ether XX. Alternatively, Mitsunobu reaction with the alcohol derivative of XIX also yield XX. The group X-Q in XX can then be transformed to another X-Q group to afford another example of II.

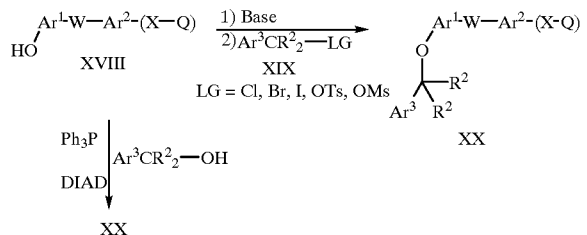

Method E

The aryl bromide, iodide or triflate XXI can be coupled with an alkyne or the alkene XXIII in the presence of a catalyst such as $Pd(OAc)_2$ (J. Org. Chem. 1979, 4078) to give the products XXII or XXIV respectively. Catalytic hydrogenation of the alkyne XXII over Lindlar's catalyst can afford the cis alkene XXV. When R=H, compounds XXII, XXIV and XXV are substructures of II and they can be treated as in method B to yield other examples of II.

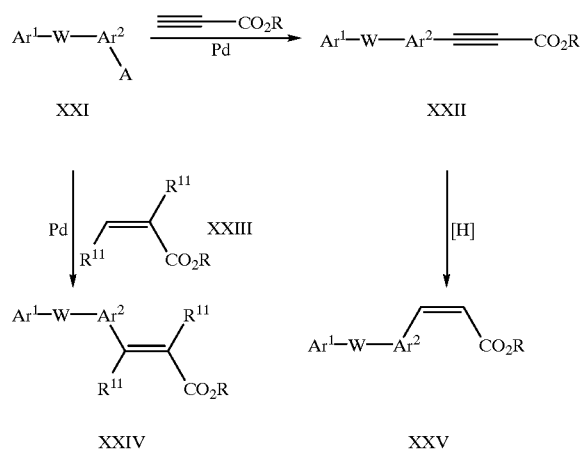

Method F

An aryl thiol, alcohol or amine XXVI can be treated with a base and then with reagent XXVII to yield the derivative XXVIII. The group E'-F-Q can be transformed to another E'-F-Q group using the other methods described here and yield examples of II possessing an heteroatom attached to $Ar^2$ in the linker X

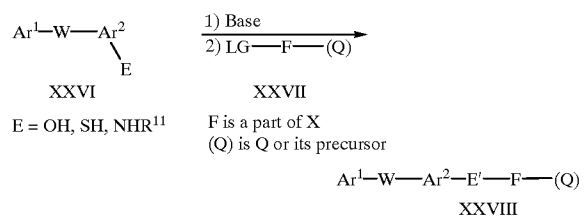

Method G

Compounds II possessing a cyclopropane unit as an X group XXX can be synthesized via a reaction between the alkene XX and a diazoacetate in the presence of a catalyst such as rhodium acetate dimer.

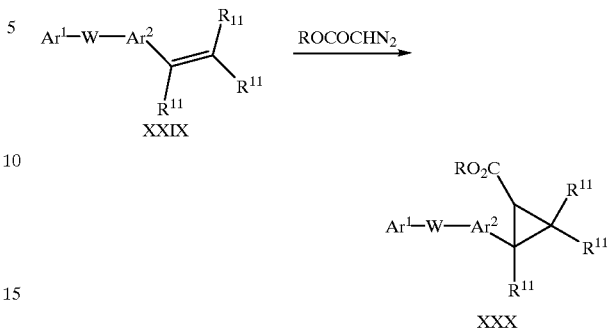

Method H

Compounds II possessing a double bond as part of the linker X can be synthesized via a Wittig reaction as exemplified in the next scheme. Phosphonium salts XXII and XXIV can be obtained from the corresponding Ar—$CHR^9$—LG by reaction with $Ph_3P$.

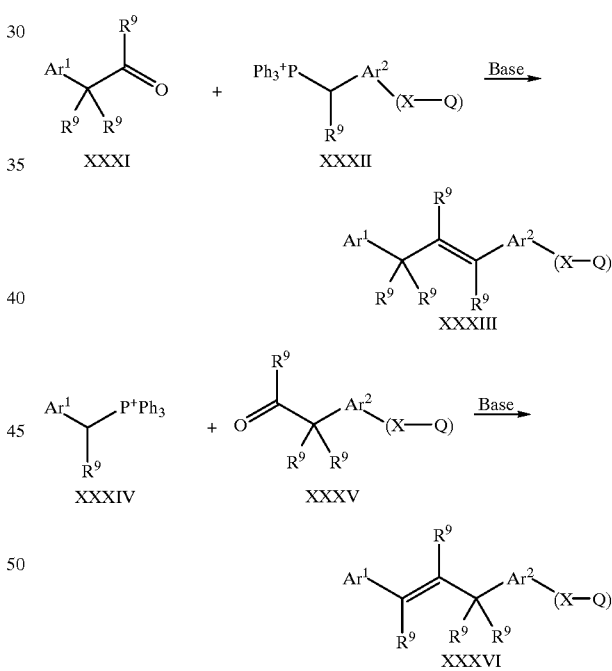

Method I

Compounds II possessing two heteroatoms as part of the linker W as in XL can be synthesized from a reagent containing two leaving groups XXXVII and two aromatics W compounds containing an alcohol, an amine or a thiol function E as described in the following scheme.

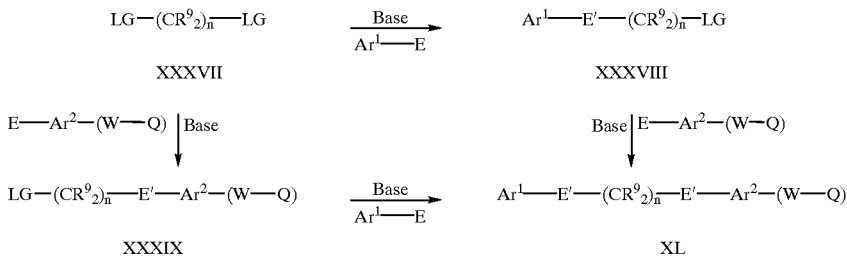

Method J

Compounds II possessing one heteroatom as part of the linker W as in XLV can be synthesized from a reagent containing one leaving group XLII or XLIII and an aromatic compound containing an alcohol, an amine or a thiol function E (XLI or XLIV) as described in the following two equations.

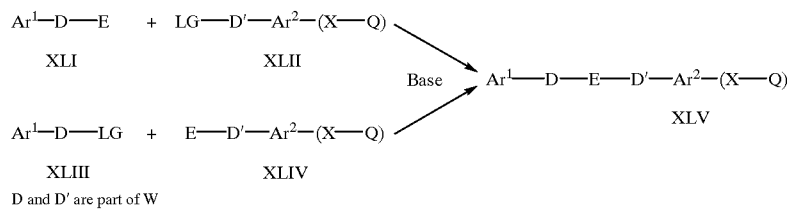

D and D' are part of W

Assays for Determining Biological Activity

The compound of Formula II can be tested using the following assays to determine their prostanoid antagonist or agonist activity in vitro and in vivo and their selectivity. The prostaglandin receptors investigated were DP, $EP_1$, $EP_2$, $EP_3$, $EP_4$, FP, IP and TP.

Stable Expression of Prostanoid Receptors in the Human Embryonic Kidney (HEK) 293(ebna) Cell Line Prostanoid receptor cDNAs corresponding to full length coding sequences were subcloned into the appropriate sites of mammalian expression vectors and transfected into HEK 293(ebna) cells. HEK 293(ebna) cells expressing the individual cDNAs were grown under selection and individual colonies were isolated after 2–3 weeks of growth using the cloning ring method and subsequently expanded into clonal cell lines.

Prostanoid Receptor Binding Assays

HEK 293(ebna) cells are maintained in culture, harvested and membranes are prepared by differential centrifugation, following lysis of the cells in the presence of protease inhibitors, for use in receptor binding assays. Prostanoid receptor binding assays are performed in 10 mM MES/KOH (pH 6.0) (EPs, FP and TP) or 10 mM HEPES/KOH (pH 7.4) (DP and IP), containing 1 mM EDTA, 10 mM divalent cation and the appropriate radioligand. The reaction is initiated by addition of membrane protein. Ligands are added in dimethylsulfoxide which is kept constant at 1% (v/v) in all incubations. Non-specific binding is determined in the presence of 1 $\mu$M of the corresponding non-radioactive prostanoid. Incubations are conducted for 60 min at room temperature or 30° C. and terminated by rapid filtration. Specific binding is calculated by subtracting non specific binding from total binding. The residual specific binding at each ligand concentration is calculated and expressed as a function of ligand concentration in order to construct sigmoidal concentration-response curves for determination of ligand affinity.

Prostanoid Receptor Agonist and Antagonist Assays

Whole cell second messenger assays measuring stimulation ($EP_2$, $EP_4$, DP and IP in HEK 293(ebna) cells) or inhibition ($EP_3$ in human erythroleukemia (HEL) cells) of intracellular cAMP accumulation or mobilization of intracellular calcium ($EP_1$, FP and TP in HEK 293(ebna) cells stably transfected with apo-aequorin) are performed to determine whether receptor ligands are agonists or antagonists. For cAMP assays, cells are harvested and resuspended in HBSS containing 25 mM HEPES, pH 7.4. Incubations contain 100 $\mu$M RO-20174 (phosphodiesterase type IV inhibitor, available from Biomol) and, in the case of the $EP_3$ inhibition assay only, 15 $\mu$M forskolin to stimulate cAMP production. Samples are incubated at 37° C. for 10 min, the reaction is terminated and cAMP levels are then measured. For calcium mobilization assays, cells are charged with the co-factors reduced glutathione and coelenterazine, harvested and resuspended in Ham's F12 medium. Calcium mobilization is measured by monitoring luminescence provoked by calcium binding to the intracellular photoprotein aequorin. Ligands are added in dimethylsulfoxide which is kept constant at 1% (v/v) in all incubations. For agonists, second messenger responses are expressed as a function of ligand concentration and both $EC_{50}$ values and the maximum response as compared to a prostanoid standard are calculated. For antagonists, the ability of a ligand to inhibit an agonist response is determined by Schild analysis and both KB and slope values are calculated.

Rat Paw Edema Assay

The method is the same as described in Chan et at (J. Pharmacol. Exp. Ther. 274: 1531–1537, (1995)).

LPS-Induced Pyrexia in Conscious Rats

The method is the same as described in Chan et at (J. Pharmacol. Exp. Ther. 274: 1531–1537, (1995)).

LPS-Induced Pyrexia in Conscious Squirrel Monkeys

The method is the same as described in Chan et at (Eur. J. Pharmacol. 327: 221–225, (1997)).

Acute Inflammatory Hyperalgesia Induced by Carrageenan in Rats

The method is the same as described in Boyce et at (Neuropharmacology 33: 1609–1611, (1994)).

Adjuvant-Induced Arthritis in Rats

Female Lewis rats (body weight ~146–170 g) were weighed, ear marked, and assigned to groups (a negative control group in which arthritis was not induced, a vehicle control group, a positive control group administered indomethacin at a total daily dose of 1 mg/kg and four groups administered with a test compound at total daily doses of 0.10–3.0 mg/kg) such that the body weights were equivalent within each group. Six groups of 10 rats each were injected into a hind paw with 0.5 mg of *Mycobacterium butyricum* in 0.1 mL of light mineral oil (adjuvant), and a negative control group of 10 rats was not injected with adjuvant. Body weights, contralateral paw volumes (determined by mercury displacement plethysmography) and lateral radiographs (obtained under Ketamine and Xylazine anesthesia) were determined before (day −1) and 21 days following adjuvant injection, and primary paw volumes were determined before (day −1) and on days 4 and 21 following adjuvant injection. The rats were anesthetized with an intramuscular injection of 0.03–0.1 mL of a combination of Ketamine (87 mg/kg) and Xylazine (13 mg/kg) for radiographs and injection of adjuvant. The radiographs were made of both hind paws on day 0 and day 21 using the Faxitron (45 kVp, 30 seconds) and Kodak X-OMAT TL film, and were developed in an automatic processor. Radiographs were evaluated for changes in the soft and hard tissues by an investigator who was blinded to experimental treatment. The following radiographic changes were graded numerically according to severity: increased soft issue volume (0–4), narrowing or widening of joint spaces (0–5) subchondral erosion (0–3), periosteal reaction (0–4), osteolysis (0–4) subluxation (0–3), and degenerative joint changes (0–3). Specific criteria were used to establish the numerical grade of severity for each radiographic change. The maximum possible score per foot was 26. A test compound at total daily doses of 0.1, 0.3, 1, and 3 mg/kg/day, indomethacin at a total daily dose of 1 mg/kg/day, or vehicle (0.5% methocel in sterile water) were administered per os b.i.d. beginning post injection of adjuvant and continuing for 21 days. The compounds were prepared weekly, refrigerated in the dark until used, and vortex mixed immediately prior to administration.

EXAMPLES

The invention is further illustrated in the following non-imiting examples in which, unless otherwise stated:

- yields are given for illustration only and are not necessarily the maximum attainable;
- all the end products of the formula II were analyzed by NMR, TLC and mass spectrometry;
- intermediates were all analyzed by NMR and TLC; most compounds were purified by flash chromatography on silica gel, recrystallization and/or swish (suspension in a solvent followed by filtration of the solid) with a solvent such as ether:hexane 1:1;
- the course of reactions was followed by thin layer chromatography (TLC) and reaction times are given for illustration only;
- temperatures are in degrees Celsius.

Example 1

3-(2-(3-(2-(benzyloxy)-3-methylphenyl)propyl) phenyl)propanoic acid

A mixture of the products of examples 28 and 29 was dissolved in 2 ml MeOH:EtOAc 1:1 with tris (triphenylphosphine)rhodium(I) chloride (2 mg) and the mixture hydrogenated under 60 psi of $H_2$. The reaction was followed by mass spectroscopy and, when completed, the solvent was evaporated and the product purified by flash chromatography with EtOAc:toluene containing 1% AcOH.

MS (APCI, neg.) 387.2 (M−1), 279.2.

Examples 2 and 3

N2-((E)-3-(2-((E)-3-(2-(benzyloxy)-3-methylphenyl)-1-propenyl)phenyl)-2-propenoyl)-2-thiophenesulfonamide and N2-((E)-3-(2-((E)-3-(2-(benzyloxy)-3-methylphenyl)-2-propenyl)phenyl)-2-propenoyl)-2-thiophenesulfonamide These acylsulfonamides were prepared from the cinnamic acids of examples 28 and 29 following the procedure of examples 44 and 45.

MS (APCI, neg.) 528.2 (M−1).

Examples 6 and 7

Sodium(E)-3-(2-((E)-3-(2-(benzyloxy)phenyl)-1-propenyl)phenyl)-2-propenoate and Sodium(E)-3-(2-((E)-3-(2-(benzyloxy)phenyl)-2-propenyl) phenyl)-2-propenoate Step 1 1-allyl-2-(benzyloxy)benzene Sodium hydride 80% in oil (800 mg, 1.2 equiv.) was added to a solution of 2-allylphenol (2.998 g, 22 mmol) in DMF (40 ml) at 0 C. and the mixture was stirred at 0° C. for 15 min. and at r.t. for 1 h. Benzyl bromide (2.9 ml, 1.1 equiv.) was then added and the stirring was continued for 1 h. After hydrolysis with saturated $NH_4Cl$, the product was extracted in EtOAc, dried over $Na_2SO_4$, and concentrated to yield 5.01 g of an oil (yield 100%).

$^1$H NMR (Acetone-$d_6$) δ 3.40 (2H, d), 4.95–5.08 (2H, m), 5.13 (2H, s), 6.00 (1H, m), 6.90 (1H, dd), 7.03 (1H, d), 7.18 (2H, m), 7.32 (1H, m), 7.40 (2H, dd), 7.50 (2H, d).

Step 2 (E)-3-(2-((E)-3-(2-(benzyloxy)phenyl)-1-propenyl) phenyl)-2-propenoic acid and (E)-3-(2-((E)-3-(2-(benzyloxy)phenyl)-2-propenyl)phenyl)-2-laropenoic acid A mixture containing 2-bromocinnamic acid (250 mg, 1.10 mmol), the product of step 1 (271 mg, 1.1 equiv.), $Pd(OAc)_2$ (8 mg, 0.03 equiv.), LiCl (47 mg, 1 equiv.), LiOAc (280 mg, 2.5 equiv.) and $Bu_4NCl$ (611 mg, 2 equiv.) in DMF (2 ml) was degassed and heated to 100 C. o.n. 0.5 N HCl was then added and the product was extracted in EtOAc, washed with 0.5 N HCl, dried over $Na_2SO_4$ and concentrated to dryness. Recrystallization from ether:hexane afforded the title product as a white solid. Yield: 251 mg, 62%.

$^1$H NMR (Acetone-$d_6$) δ 3.68 and 3.74 (2H, 2d), 5.10 and 5.20 (2H, 2s), 6.30–6.53 (2H, m), 6.70–6.93 (2H, m), 7.03 (1H, 2d), 7.18 (1H, m), 7.25–7.43 (7H, m), 7.50 (2H, m), 7.68 and 7.77 (1H, 2d), 8.03 (1H, 2d).

Step 3

The acids of step 2 were dissolved in EtOH and 1.0 equiv. of NaOH 1.0 N was added. The solvent was evaporated, the oil dissolved in water and the products were freeze-dried to afford a white solid.

MS (APCI, neg.) 369.0 (M−1)

The products of the following examples have been prepared in a manner similar to examples 6 and 7 and are mixtures of 2 compounds each.

| Examples | Note | MS (APCI, neg.)[c] |
|---|---|---|
| 8 & 9 | | 429.1 |
| 10 & 11 | d | 411.2 |
| 12 & 13 | | 399.1 |
| 14 & 15 | | 399.1 |
| 16 & 17 | a | 371.1, 327.2 (M-CO$_2$H) |
| 18 & 19 | a | 405.2, 361.0 (M-CO$_2$H) |
| 21 & 22 | d | 443.1 |
| 23 & 24 | d | 307.1 |
| 25 & 26 | d | 263.1, 219.1 (M-CO$_2$H) |
| 28 & 29 | b | 383.2 |
| 38 & 39 | d | 293.1, 234.0 |
| 40 & 41 | d | 323.1, 264.1 |
| 72 & 73 | | 368.9, 233.2 |

[a] Pd coupling (step 2) at 120° C. o.n.,
[b] the two products were separated by HPLC on a NovaPak C18 column,
[c] M-1
[d] the sodium salt was not prepared Example 20

2-(2-(3-(4-(benzyloxy)-3-methoxyphenyl)propyl)phenyl)cyclopropane carboxylic acid Step 1 (E)-2-(2-(3-(4-(benzyloxy)-3-methoxyphenyl)propyl)phenyl)-2-propenoic acid A solution of 9-borabicyclo[3.3.1]nonane 0.5 M in THF (3.8 ml, 1.5 equiv.) was added slowly to 4-allyl-1-benzyloxy-2-methoxybenzene (257 mg, 1.21 mmol, prepared as in examples 6 and 7, step 1) and the mixture was stirred at r.t. for 30 min. K$_3$PO$_4$ (384 mg), 2-bromocinnamic acid (222 mg, 978 mmol), (1,1'-bis(diphenylphosphino)ferrocene)dichloropalladium(II) (31 mg) and DMF (4 ml) were added and the mixture was degassed and stirred at 50° C. o.n. A saturated solution of NH$_4$Cl was added, the solution was acidified with AcOH and the product was extracted in EtOAc, dried over Na$_2$SO$_4$ and partially purified by flash chromatography with EtOAc:toluene:AcOH 5:95:1.

Step 2 Methyl 2-(2-(3-(4-(benzyloxy)-3-methoxyphenyl)propyl)phenyl)cyclopropane-carboxylate The acid of step 1 was treated with diazomethane in ether at reflux. The solvent was removed and the ester was purified by flash chromatography with EtOAc:toluene 2.5:97.5.

Step 3

The ester of step 2 was hydrolyzed with NaOH as in example 61, step 3. The final product was purified by HPLC with EtOAc:toluene:AcOH 2.5:97.5:1 on a μPorasil column to yield the title cyclopropaneacetic acid.

1H NMR (acetone, d$_6$) δ 1.43 (2H, m), 1.76 (1H, m), 1.93 (2H, m), 2.55 (1H, m), 2.65 (2H, t), 2.82 (2H, m), 3.80 (3H, s), 5.07 (2H, s), 6.72 (1H, d), 6.87 (1H, s), 6.91 (1H, d), 7.03 (1H, d), 7.08–7.22 (3H, m), 7.28–7.41 (3H, m), 7.47 (2H, d). MS (APCI, neg.) 415.1 (M-1), 324.3.

Example 27

(E)-3-(2-((E)-3-(2-hydroxy-3-methylphenyl)-2-propenyl)phenyl)-2-propenoic acid

This product was obtained as a mixture with the other isomer (E)-3-(2-((E)-3-(2-hydroxy-3-methylphenyl)-1-propenyl)-2-propenoic acid via a palladium coupling between 2-bromocinnamic acid and 2-alkyl-6-methylphenol as in examples 6 and 7, step 2. The title acid was separated from the other isomer by recrystallization from ether:hexane 1:1. Yield of pure product: 48%.

1H NMR (Acetone-d$_6$) δ 2.20 (3H, s), 3.74 (2H, d), 6.34 ((1H, m), 6.44 (1H, d), 6.70 (1H, t), 6.80 (1H, d), 6.95 (1H, d), 7.22 (1H, d), 7.30 (1H, t), 7.35 (2H, m), 7.74 (1H, d), 8.10 (1H, d).

Examples 30 and 31

(E)-3-(2-((E)-3-(2-((7-chloro-2-quinolinyl)methoxy)-3-methylphenyl)-1-propenyl)phenyl)-2-propenoic acid and (E)-3-(2-((E)-3-(2-((7-chloro-2-quinolinyl)methoxy)-3-methylphenyl)-2-propenyl)phenyl)-2-propenoic acid Step 1 Methyl(E)-3-(2-((E)-3-(2-hydroxy-3-methylphenyl)-2-propenyl)phenyl)-1-propenyl)phenyl)-2-propenoate and methyl (E)-3-(2-((E)-3-(2-hydroxy-3-methylphenyl)-2-propenyl)phenyl)-2-propenyl)phenyl)-2-propenoate These two products were prepared as a mixture via esterification of the two acids in example 27 using the procedure of example 61, step 1.

Step 2

Treatment of the two esters of step 1 with 7-chloro-2-(bromomethyl)quinoline (obtained by bromination of 7-chloroquinaldine with N-bromosuccinimide) and hydrolysis of the esters was performed as in example 61, steps 2 and 3.

MS (APCI, neg.) 470.0, 468.0 (M-1).

Example 32

2-(3-(2-benzyloxy-3-methylphenyl)propyl)benzoic acid

3-Allyl-2-(benzyloxy)toluene (prepared as in examples 6 and 7, step 1) was treated with 9-BBN and then with ethyl 2-bromobenzoate as in example 20, step 1, to give the ester of the title compound. This ester was hydrolyzed as in example 61, step 3.

1H NMR (acetone d$_6$) δ 1.95 (2H, m), 2.30 (3H, s), 2.75 (2H, m), 3.08 (2H, dd), 4.70 (2H, s), 6.92–7.12 (3H, m), 7.24–7.53 (8H, m), 7.93 (1H, d).

Examples 33 and 34

Sodium 2-(3-(2-benzyloxy-3-methylphenyl)-1-propenyl)benzoate and Sodium 2-(3-(2-benzyloxy-3-methylphenyl)-2-propenyl)benzoate 3-allyl-2-(benzyloxy)toluene (prepared as in examples 6 and 7, step 1) was coupled to ethyl 2-bromobenzoate as in examples 6 and 7, step 2. The resulting ester was hydrolyzed as in example 61, step 3.

1H NMR (acetone d$_6$) δ 2.25 and 2.32 (3H, 2s), 3.64 and 3.97 (2H, 2d), 4.76 and 4.93 (2H, 2s), 6.33 and 6.50 (1H, 2td), 6.68–7.64 (12H, m), 7.90 and 7.98 (1H, 2d).

The sodium salts were prepared as in examples 6 and 7, step 3.

Example 35

Sodium(E)-3-(2-(3-(2-benzyloxy-3-methylphenyl)propyl)phenyl)-2-propenoate

Step 1 2-(3-(2-benzyloxy-3-methylphenyl)propyl)benzaldehyde 3-allyl-2-(benzyloxy)toluene was treated with 9-BBN and then with 2-bromobenzaldehyde as in example 20, step 1, to give the title aldehyde. Yield 58%.

Step 2 Ethyl(E)-3-(2-(3-(2-benzyloxy-3-methylphenyl)propyl)phenyl)-2-propenoate

To the aldehyde of step 1 (850 mg, 2.47 mmol) was added (methoxycarbonylmethylene)triphenylphosphorane (1.24 g, 1.5 equiv.) and the mixture was heated to 80 C. in 25 ml of toluene for 10 h. NH$_4$Cl was added and the mixture was extracted in EtOAc, dried over Na$_2$SO$_4$ and the product was purified by flash chromatography with EtOAc:toluene 2.5:97.5. Yield: 770 mg, 78%.
Step 3
Hydrolysis of the ester was performed as in example 61, step 3.
MS (APCI, neg.) 385.1 (M−1).
The sodium salt was prepared as in examples 6 and 7, step 3.
The products of the following table were prepared in a manner similar to example 34.

| Example # | MS (APCI, neg.) |
|---|---|
| 36 | 401.2 (M−1), 310.0 |
| 37 | 401.2 (M−1), 310.0 |

Example 42

Sodium(E)-3-(2-((E)-3-(2-(benzyloxy)phenyl)-3-hydroxy-1-propenyl)phenyl)-2-propenoate Step 1 1-(2-(benzyloxy)phenyl)-2-propen-1-ol 2-(benzyloxy)benzaldehyde (5g, 23.6 mmol) was reacted with vinylmagnesium bromide in THF (90 ml) at 0 C. The reaction was quenched with 2 N HCl and the product was extracted in i-PrOAc, dried over $Na_2SO_4$ and purified by flash chromatography with EtOAc:toluene 2.5:97.5.
Step 2
A mixture containing the allylic alcohol of step 1 (298 mg, 1.24 mmol), 2-bromocinnamic acid (299 mg, 1.06 equiv.), $Bu_4NOAc$ (380 mg, 1 equiv.), $Et_3N$ (1.2 ml), $PdCl_2(Ph_3P)_2$ (26 mg, 0.03 equiv.) and DMF (5 ml) was degassed and heated to 100 C. for 2 h. After addition of $NH_4Cl$ and acidification with AcOH, the product was extracted in EtOAc, dried over $Na_2SO_4$ and purified by flash chromatography with EtOAc:toluene:AcOH 10:90:5. Yield: 239 mg, 50%.
MS (APCI, neg.) 385.1 (M−1), 235.0
The sodium salt was prepared as in examples 6 and 7, step 3.

Example 43

N2-((E)-3-(2-(3-(2-(benzyloxy)-3-methylphenyl) propyl)phenyl)-2-propanoyl)-2-thiophenesulfonamide, Sodium salt The mixture of the two acylsulfonamides of examples 2 and 3 were reduced by catalytic hydrogenation using 10% Pd/C in EtOAc at atmospheric pressure for 3 days. Filtration through celite and purification by flash chromatography yielded the title sulfonamide.
$^1$H NMR (Acetone-$d_6$) δ 1.85 (2H, m), 2.30 (3H, s), 2.60 (4H, m), 2.71 (2H, t), 2.85 (2H, t), 4.70 (2H, s), 6.92–7.13 (7H, m), 7.20 (1H, dd), 7.30–7.50 (5H, m), 7.80 (1H, d), 7.95 (1H, d). MS (APCI, neg.) 531.9 (M−1).
The sodium salt was prepared as in examples 6 and 7, step 3.

Examples 44 and 45

N2-((E)-3-(2-((E)-3-(4-(benzyloxy)-3-methoxyphenyl)-1-propenyl)phenyl)-2-propenoyl)-2-thiophenesulfonamide and N2-((E)-3-(2-((E)-3-(4-(benzyloxy)-3-methoxyphenyl)-2-propenyl)phenyl)-2-propenoyl)-2-thiophene sulfonamide, Sodium salts The product of examples 14 and 15 (254 mg, 634 μmol) was dissolved in 6 ml $CH_2Cl_2$. DMF (10 μl) and oxalyl chloride (76 ml, 1.4 equiv.) were then added at 0 C. and the solution was stirred at r.t. for 1.5 h. The solvent was evaporated and the resulting acid chloride was redissolved in $CH_2Cl_2$ (6 ml). At 0 C. , 2-thiophenesulfonamide (124 mg, 1.2 equiv.) and $Et_3N$ (177 μl, 2 equiv.) were added and the mixture was stirred at 0 C. for 1 h. 0.5 N HCl was then added and the product was extracted in i-PrOAc, dried over $Na_2SO_4$ and purified by flash chromatography on silica using EtOAc:toluene:AcOH 20:80:1. Yield: 201 mg, 58%.
MS (APCI, neg.) 544.2 (M−1).
The sodium salts were prepared as in examples 6 and 7, step 3.

Examples 46 and 47

Sodium(E)-3-(2-((2-(2-(benzyloxy)-3-methylphenyl) cyclopropyl)methyl)phenyl)-2-propenoate and Sodium(E)-3-(2-(2-((2-(benzyloxy)-3-methylphenyl) methyl)cyclopropyl)phenyl)-2-propenoate Step 1 Ethyl 2-((2-(2-(benzyloxy)-3-methylphenyl) cyclopropyl)methyl)benzoate and ethyl 2-(2-((2-(benzyloxy)-3-methylphenyl)methyl)cyclopropyl)benzoate The intermediate ester of example 33 was treated with portions of $CH_2N_2$ solution in ether and $Pd(OAc)_2$ alternatively and at 0 C. until the reaction was complete. AcOH was added and the mixture was filtered through silica with ether and concentrated. This product was used as such in the next step.

Step 2 2-((2-(2-(benzyloxy)-3-methylphenyl)cyclopropyl) methyl)benzaldehyde and 2-(2-((2-(benzyloxy)-3-methylphenyl)methyl)cyclopronyl)benzaldehyde To a solution of the ester of step 1 (3.68 mmol) in THF (20 ml) was added diisobutylaluminum hydride 1.0 M in toluene (16 ml, 4.4 equiv.) at −72 C. and the mixture was stirred at −40 C. for 10 min. The reaction was quenched with sodium potassium tartrate 1.0 M and was stirred at r.t. for 1.5 h. It was neutralized with AcOH and extracted in i-PrOAc. The product was dried over $Na_2SO_4$ and concentrated.

This benzylic alcohol was oxidized with activated $MnO_2$ (20 equiv.) in EtOAc at r.t. o.n. The mixture was then filtered through celite, concentrated and the aldehyde was purified by flash chromatography with toluene. Yield: 83% for steps 1 and 2.
Step 3
The aldehyde of step 2 was treated as in Example 34, steps 2 and 3, to afford the two title products. The sodium salts were prepared as in examples 6 and 7, step 3.
MS (APCI, neg.) 397.1 (M−1).

Example 48

Sodium(E)-3-(2-((E) -3-(2-benzyloxy-3-methylphenyl)-3-hydroxy-1-propenyl)phenyl)-2-propenoate Step 1 Methyl(E)-3-(2-((E)-3-(2-benzyloxy-3-methyliphenyl)-3-acetoxy-1-propenyl)phenyl)-2-propenoate and methyl(E)-3-(2-((E)-3-(2-benzyloxy-3-methyliphenyl)-1-acetoxy-2-propenyl)phenyl)-2-propenoate.

The two products of examples 28 and 29 were esterified with NaH and MeI as in example 61, step 1. These esters (928 mg, 2.33 mmol) were heated to reflux in AcOH (15 ml) with $SeO_2$ (310 mg, 1.2 equiv.) for 15 min. After neutralization with $NaHCO_3$, the products were extracted in EtOAc, dried over $Na_2SO_4$ and purified by flash chromatography with EtOAc:toluene 5:95.

Step 2 Methyl(E)-3-(2-((E)-3-(2-benzyloxy-3-methylphenyl)-3-hydroxy-1-propenyl)phenyl)-2-propenoate The product of step 1 (2.3 mmol) was treated with 1.8-diazabicyclo[5.4.0]undec-7-ene (3 drops) in MeOH (10 ml) for 2 h. After evaporation, the title product was separated from the less polar cyclized isomer (methyl 2-(3-((E)-2-(2-(benzyloxy)-3-methylphenyl)-1-ethenyl)-1,3-dihydro-l)-isobenzofuranyl)acetate) by flash chromatography with EtOAc:toluene 2.5:97.5 and 5:95.
Step 3
Hydrolysis was performed as in example 61, step 3. The sodium salt was prepared as in examples 6 and 7, step 3.
MS (APCI, neg.) 399.1 (M−1), 249:0.

Examples 50 and 51

(E)-3-(2-((E)-3-(2-(2,6-dichlorobenzyloxy)-3-methylphenyl)-3-hydroxy-1-propenyl)phenyl)-2-propenoic acid and (E)-3-(2-((E)-3-(2-(2,6-dichlorobenzyloxy)-3-methylphenyl)-1-hydroxy-2-propenyl)phenyl)-2-propenoic acid Step 1 (E)-3-(2-((E)-3-(2-(2,6-dichlorobenzyloxy)-3-methylphenyl)-3-acetoxy-1-propenyl)phenyl)-2-propenoic acid and (E)-3-(2-((E)-3-(2-(2,6-dichlorobenzyloxy)-3-methylphenyl)-1-acetoxy-2-propenyl)phenyl)-2-propenoic acid The product of example 61 was treated with $SeO_2$ in AcOH as in example 48, step 1 to afford the two title acetates. Yield: 92%.
Step 2
The two acetates of step 1 (153 mg, 282 μmol) were heated in $AcOH:H_2O$ 1:1 (14 ml) at 105 C. for 45 min. After addition of $NH_4Cl$, the products were extracted in EtOAc, dried over $Na_2SO_4$ and purified by flash chromatography with EtOAc:toluene:AcOH 10:90:1. The two products were separated by HPLC on a NovaPak C18 cartridge using MeOH:(1:1 AcOH:AcONa 2 g/L) 7:3 and UV detection at 280 mm. The more polar product was (E)-3-(2-((E)-3-(2-(2,6-dichlorobenzyloxy)-3-methylphenyl)-1-hydroxy-2-propenyl)phenyl)-2-propenoic acid. Yield: 28 mg.
$^1$H NMR (acetone $d_6$) δ 2.10 (3H, s), 5.20 (2H, s), 5.73 (1H, d), 6.20 (1H, d), 6.47 (1H, dd), 6.97 (1H, t), 7.04 (1H, d), 7.10 (1H, d), 7.37–7.48 (6H, m), 7.63 (1H, d), 7.72 (1H, d), 8.35 (1H, d). MS (APCI, neg.) decomposition.
The less polar isomer was (E)-3-(2-((E)-3-(2-(2,6-dichlorobenzyloxy)-3-methylphenyl)-3-hydroxy-1-propenyl)phenyl)-2-propenoic acid.
Yield: 17 mg.
MS (APCI, neg.) 467.0 (M−1), 291.0.

Examples 58 and 59

(E)-3-(2-((E)-3-(2-(2,6-dichlorobenzyloxy)-3-(hydroxymethyl)phenyl)-1-propenyl)phenyl)-2-propenoic acid and (E)-3-(2-((E)-3-(2-(2,6-dichlorobenzyloxy)-3-(hydroxymethyl)phenyl)-2-propenyl)phenyl)-2-propenoic acid Step 1 3-allyl-2-(2,6-dichlorobenzyloxy)benzaldehyde
2-(allyloxy)benzaldehyde (2.00 g, 12.33 mmol) was heated in o-dichlorobenzene (20 ml) at reflux o.n. The mixture was poured on top of a flash chromatography column and eluted with toluene:hexane 1:1.
Yield: 1.346 g, 67%.
Step 2
The phenol of step 1 was treated with NaH and 2,6-dichlorobenzyl bromide as in examples 6 and 7, step 1, to give the benzyl ether. Then, the aldehyde was reduced with diisobutylaluminum hydride in THF at −10 C. for 15 min. (see examples 46 and 47, step 2). Finally, a palladium coupling with 2-bromocinnamic acid was performed as in examples 6 and 7, step 2, to give the two title isomers.

Overall yield: 65%.
MS(APCI, neg.) 467.1 (M−1), 291.1.

Example 61

Sodium(E)-3-(2-((E)-3-(2-(2,6-dichlorobenzyloxy)-3-methylphenyl)-2-propenyl)phenyl)-2-propenoate Step 1 Methyl(E)-3-(2-((E)-3-(2-hydroxy-3-methylphenyl)-2-propenyl)phenyl)-2-propenoate
The product of example 27 (2.001 g, 6.80 mmol) was dissolved in DMF (14 ml) and NaH 80% in oil (244 mg, 1.2 equiv.) was added at 0 C. The mixture was stirred for an hour at 0 C., then MeI (635 μl, 1.5 equiv.) was added and the stirring continued for 2 h. After hydrolysis with 0.5 N HCl, the product was extracted in EtOAc and purified by flash chromatography on silica with EtOAc:toluene 2.5:97.5 and 5:95. Yield: 1.70 g, 81%.
Step 2 Methyl(E)-3-(2-((E)-3-(2-(2,6-dichlorobenzyloxy)-3-methylphenyl)-2-proyenyl)phenyl)-2-propenoate
The product of step 1 was treated with NaH and 2,6-dichlorobenzyl bromide as in examples 6 and 7, step 1, to afford the dichlorobenzyl ether.
Step 3
The ester (1.01 g, 2.18 mmol) was hydrolyzed with NaOH 10 N (930 μl) in $THF:MeOH:H_2O$ 4:2:1 (28 ml) at r.t. o.n. The reaction was quenched with sat. $NH_4Cl$, acidified with acetic acid and the product was extracted in EtOAc, concentrated and recrystallized in 20 ml ether:hexane 1:1. Yield: 746 mg, 75%.
The sodium salt was prepared as in examples 6 and 7, step 3.
MS (APCI, neg.) 452.0, 451.0 (M−1), 275.2.
The following compounds were prepared as in example 61.

| Example # | MS (APCI, neg.)[a] |
|---|---|
| 28 | 383.2 |
| 53 | 401.1, 275.2 |
| 55 | 419.1, 275.2 |
| 57 | 419.1, 275.2 |
| 63 | 451.1, 275.2 |
| 65 | 449.1, 275.2 |

[a]M-1.

Example 70

Sodium(E)-3-(2-(3-phenoxybenzyloxymethyl)phenyl)-2-propenoate

Step 1 Ethyl(E)-3-[2-(bromomethyl)phenyl]-2-propenoate
To a suspension of ethyl(E)-3-(2-methylphenyl)-2-propenoate (20.0 g; 105 mmol) and NBS (19.64 g; 110.3 mmol) in refluxing $CCl_4$ was added benzoyl peroxide (1.27 g) and the mixture was stirred for 12 h. The solution was cooled to r.t., filtered and concentrated. Flash chromatography with EtOAc:hexane 5:95 yielded the title compound (14.18 g, 50%).
$^1$H NMR ($CDCl_3$) δ 1.30 (3H, t), 4.25 (2H, q), 4.60 (2H, s), 6.45 (1H, d), 7.30 (3H, m), 7.57 (1H, m) and 8.05 (1H, d).
Step 2 Ethyl(E)-3-(2-((3-phenoxy)benzyloxy)phenyl)-2-propenoate
To a solution of 3-phenoxybenzylalcohol (545 mg; 2.72 mmol) in DMF (5 ml) was added NaH (92 mg; 3.1 mmol; 80% dispersion in oil) and ethyl(E)-3-(2-(bromomethyl)phenyl)-2-propenoate (810 mg; 3.0 mmol). After 6 h at r.t., 20 mg extra NaH was added. The final mixture was stirred at r.t. for 10 h then quenched using 0.3 ml of AcOH. The mixture was diluted with Et$_2$O (25 ml), washed with water (3×20 ml) and brine, dried over MgSO$_4$ and concentrated. Flash chromatography with EtOAc:toluene 5:95 afforded the desired material.

Yield: 822 mg, 78%.

Step 3

The ester of step 2 was hydrolyzed as in example 61, step 3, to yield the title acid. The sodium salt was prepared as in examples 6 and 7, step 3.

MS (APCI, neg.) 359.0 (M−1).

Example 71

Sodium(E)-3-(2-(2-phenoxybenzyloxymethyl) phenyl)-2-propenoate

This product was prepared as in example 70 from 2-phenoxybenzyl alcohol.

MS (APCI, neg.) 359.0 (M−1).

Example 74

Sodium(E)-3-(2-(3-(2-benzyloxyphenoxy)propoxy) phenyl)-2-propenoate

Step 1 Methyl(E)-3-(2-(3-bromopropoxy)phenyl)-2-propenoate

To a solution of methyl 2-hydroxycinnamate (1.31 g; 7.33 mmol) in 50 ml acetone was added 1,3-dibromopropane (1.50 ml; 14.8 mmol) and K$_2$CO$_3$ (4.36 g; 13.4 mmol). The mixture was heated to reflux for 12 h, cooled to r.t, diluted with hexane (50 ml), filtered and finally concentrated to afford the title product (1.96 g; 50% pure), which was used as such in the next step.

Step 2

2-Benzyloxyphenol (obtained from catechol, NaH, and benzyl bromide as in examples 6 and 7, step 1) was treated with NaH and the product of step 1 as in examples 6 and 7, step 1 to afford the ester of the title product. This ester was hydrolyzed as in example 61, step 3 to yield the acid. The sodium salt was prepared as in examples 6 and 7, step 3.

MS (APCI, neg.) 403.1 (M−1), 233.1, 207.1.

Example 75

Sodium(E)-3-(2-((E)-3-(2-(1-phenylethoxy)-3-methylphenyl)-2-propenyl)phenyl)-2-propenoate 1-Phenylethanol was obtained by reduction of acetophenone with NaBH$_4$ in THF:MeOH. It was then reacted with the ester of example 61, step 1, via a Mitsunobu reaction (DIAD, Ph$_3$P, THF:CH$_2$Cl$_2$, Synth. Commun. 1994, 24, 1049), to yield the ester of the title compound. This ester was hydrolyzed as in example 61, step 3, to give the title acid.

The sodium salt was prepared as in examples 6 and 7, step 3.

MS (APCI, neg.) 397.1 (M−1), 293.0, 275.3, 233.2.

Examples 77 and 78

Sodium(E)-3-(2-((E)-3-(3-phenoxyphenyl)-1-propenyl)phenyl)-2-propenoate and Sodium(E)-3-(2-((E)-3-(3-phenoxyphenyl)-2-propenyl)phenyl)-2-propenoate Step 1 1-bromo-3-phenoxybenzene To a solution of phenol (5.08 g; 54 mmol) in 30 ml dry DMF at 0 C. was added portionwise NaH (1.98 g; 66 mmol; 80% dispersion in oil). The mixture was stirred 30 min at r.t. then 1,3-dibromobenzene (33 ml; 273 mmol) and Cu$_2$O (3.95 g; 28 mmol) were added. The final mixture was heated to reflux for 4 h, cooled to r.t., diluted with Et$_2$O (200 ml), washed with water (3×200 ml), NaOH (1.0 M; 2×100 ml) and brine, dried over MgSO$_4$ and concentrated. Flash chromatography with hexane afforded the desired material.

Yield: 7.62 g, 57%.

Step 2 1-allyl-3-phenoxybenzene

A suspension of 1-bromo-3-phenoxybenzene (2.01 g; 8.08 mmol), PdCl$_2$(PPh$_3$)$_2$ (296 mg; 0.42 mmol), allyl tributyltin 3.13 g; 9.46 mmol), triphenylphosphine (455 mg; 1.73 mmol) and LiCl (1.39 g; 33 mmol) in 10 ml DMF was stirred at 100° C. for 3 h. After cooling to r.t the mixture was diluted with Et$_2$O (75 ml), washed with water (3×50 ml) and brine, dried over MgSO$_4$ and concentrated. Flash chromatography with hexane afforded the desired material.

Yield: 1.39g, 81%.

Step 3

Using the procedure of examples 6 and 7, steps 2 and 3, the product of step 2 was transformed to the title compounds.

MS (APCI, neg.) 355.1 (M−1), 311.2.

Examples 79 and 80

Sodium(E)-3-(2-((E)-3-(3-phenylbenzo[B]furan-7-yl)-1-propenyl)phenyl)-2-propenoate and Sodium (E)-3-(2-((E)-3-(3-phenylbenzo[B]furan-7-yl)-2-propenyl)phenyl)-2-propenoate Step 1 2-(2-bromophenoxy)-1-phenyl-1-ethanone To a solution of 2-bromophenol (8.71 g; 50.3 mmol) and bromoacetophenone (10.1 g; 50.5 mmol) in 50 ml acetone was added K$_2$CO$_3$ (7.02 g; 50.8 mmol). The mixture was heated to reflux for 10 h, cooled to r.t., filtered, diluted with EtOAc (100 ml), washed with HCl (1.0 M, 2×100 ml) and brine, dried over MgSO$_4$ and concentrated. The residual solid was recrystallized from EtOAc:hexane to afford the desired material.

Yield: 11.6 g, 79%.

Step 2 3-phenylbenzo[b]furan-7-yl-bromide

A mixture of 2-(2-bromophenoxy)-1-phenyl-1-ethanone (6.31 g) and polyphosphoric acid (285 g) was stirred at 95° C. for 6 h. The resulting solution was cooled to 50° C., poured in water (2 L), extracted with Et$_2$O (2×1 L). The combined organic extracts were washed with water (4×500 ml) and brine, dried over MgSO$_4$ and concentrated. The residual solid was filtered on a plug of silica gel using Et$_2$O. Recrystallization in hot hexane yielded the title compound (4.63g; 78%).

Step 3

Using the procedure of examples 77 and 78, steps 2 and 3, the bromide of step 2 was transformed to the title acid. The sodium salts were prepared as in examples 6 and 7, step 3. MS (APCI, neg.) 379.4 (M−1), 335.1.

Examples 81 and 82

N2-((E)-3-(2-((E)-3-phenyl-1-propenyl)phenyl)-2-propenoyl)-2-thiophenesulfonamide and N2-((E)-3-(2-((E)-3-phenyl-2-propenyl)phenyl)-2-propenoyl)-2-thiophenesulfonamide These acylsulfonamides were prepared from the cinnamic acids of examples 25 and 26 following the procedure of Synlett 1995, 1141.

MS (APCI, neg.) 408.2 (M−1).

Examples 83 and 84

N2-((E)-3-(2-((E)-3-(4-methoxyphenyl)-1-propenyl) phenyl)-2-propenoyl)-2-thiophenesulfonamide and N2-((E)-3-(2-((E)-3-(4-methoxyphenyl)-2-propenyl) phenyl)-2-propenoyl)-2-thiophenesulfonamide These acylsulfonamides were prepared from the cinnamic acids of examples 38 and 39 following the procedure of Synlett 1995, 1141.

MS (APCI, neg.) 438.1 (M−1), 233.2.

What is claimed is:

1. A compound represented by formula II:

Ar¹—W—Ar²—X—Q                II or a pharmaceutically acceptable salt or hydrate thereof, wherein:

Ar¹ is benzene, naphthalene, benzofuran or methylenedioxyphenyl, optionally substituted by $R^1$ and $R^3$;

$R^1$ is OH, $OCH_2Ar^3$, $SCH_2Ar^3$, $OAr^3$, $SAr^3$ or $NR^2CH_2Ar^3$;

$R^3$ is $R^4$, halogen, haloC$_{1-6}$alkyl, $N(R^5)_2$, CN, $NO_2$, $C(R^6)_3$, $CON(R^5)_2$, $OR^4$, $SR^4$ or $S(O)_nR^7$;

$R^4$ is H, lower alkyl, lower alkenyl, lower alkynyl, $CHF_2$ or $CF_3$;

$R^5$ is $R^4$, Ph or Bn, or two $R^5$ groups in combination with the atom to which they are attached represent a ring of up to 6 members containing carbon atoms and up to 2 heteroatoms selected from O, N and S;

$R^6$ is H, F, $CF_3$ or lower alkyl, or two $R^6$ groups may be taken together and represent a ring of up to 6 members containing carbon atoms and 0–2 heteroatoms selected from O, N and S;

$R^7$ is lower alkyl, lower alkenyl, lower alkynyl, $CHF_2$, $CF_3$, $N(R^5)_2$, $Ph(R^8)_2$ or $CH_2Ph(R^8)_2$;

$R^8$ is $R^4$, $OR^4$, $SR^4$ or halogen;

Ar³ is selected from the group consisting of benzene, pyridine, thiophene, furan, oxazole and thiazole, said group being optionally substituted with R₃;

Ar² is benzene, optionally substituted with 1–4 members selected from the group consisting of: $R^4$, $OR^4$, $SR^4$ and halogen;

W is selected from the group consisting of: $CH_2OCH_2$, $(CH_2)_3$, $CH_2CH=CH$, $CH=CHCH_2$, $CH(OH)CH=CH$, $CH=CHCH(OH)$, $CH_2C\equiv C$, $C\equiv CCH_2$ 1,2-c-Pr—$CH_2$— and —$CH_2$-1,2-c-Pr—;

X represents a linker which is attached to Ar² ortho to the attachment of W and is selected from the group consisting of: $(CH_2)_2$, $CH=CH$, $C\equiv C$ and 1,2-c-Pr;

and Q is $CO_2H$ or tetrazole.

2. A compound represented by formula II:

Ar¹—W—Ar²—X—Q                II or a pharmaceutically acceptable salt or hydrate thereof, wherein:

Ar¹ is benzene, naphthalene, benzofuran or methylenedioxyphenyl, optionally substituted with $R^1$ and $R^3$;

$R^1$ is OH, $OCH_2Ar^3$, $SCH_2Ar^3$, $OAr^3$, $SAr^3$ or $NR_2CH_2Ar^3$;

$R^3$ is $R^4$, halogen, haloC$_{1-6}$alkyl, $N(R^5)_2$, CN, $NO_2$, $C(R^6)_3$, $CON(R^5)_2$, $OR^4$, $SR^4$ or $S(O)_nR^7$;

$R^4$ is H, lower alkyl, lower alkenyl, lower alkynyl, $CHF_2$ or $CF_3$;

$R^5$ is $R^4$, Ph or Bn, or two $R^5$ groups in combination with the atom to which they are attached represent a ring of up to 6 members containing carbon atoms and up to 2 heteroatoms selected from O, N and S;

$R^6$ is H, F, $CF_3$ or lower alkyl, or two $R^6$ groups may be taken together and represent a ring of up to 6 members containing carbon atoms and 0–2 heteroatoms selected from O, N and S;

$R^7$ is lower alkyl, lower alkenyl, lower alkynyl, $CHF_2$, $CF_3$, $N(R^5)_2$, $Ph(R^8)_2$ or $CH_2Ph(R^8)_2$;

$R^8$ is $R^4$, $OR^4$, $SR^4$ or halogen;

Ar³ represents a member selected from the group consisting of: benzene, pyridine, thiophene, furan, oxazole or thiazole, said group being optionally substituted with $R^3$;

W is selected from the group consisting of: $CH_2OCH_2$, $(CH_2)_3$, $CH_2CH=CH$, $CH=CHCH_2$, $CH(OH)CH=CH$, $CH=CHCH(OH)$, $CH_2C\equiv C$ or $C\equiv CCH_2$;

Ar² is benzene, optionally substituted with $R^8$;

X represents a linker which is attached to Ar² ortho to the attachment of W and is selected from the group consisting of: $(CH_2)_2$, $CH=CH$, $C\equiv C$ and 1,2-c-Pr;

Q is $CONHSO_2ZAr^4$;

Z is a 0–2 carbon linker and is unsubstituted;

Ar⁴ is selected from the group consisting of: benzene, pyridine, thiophene, furan, oxazole, thiazole, 1,3,4-thiadiazole and naphthalene, and is optionally substituted by $R^3$.

3. A compound in accordance with claim 1 wherein:

Ar¹ is benzene substituted in position 2 or position 4 or both relative to the attachment of W with a member selected from the group consisting of: OH, $OCH_2Ar^3$, $SCH_2Ar^3$, $OAr^3$, $SAr^3$ and $NR^2CH_2Ar^3$, and is optionally substituted in position 3 with a member selected from the group consisting of: OMe, $OCHF_2$ and lower alkyl;

Ar³ is benzene or thiophene, optionally substituted with $R^8$;

W is selected from the group consisting of: $CH_2OCH_2$, $(CH_2)_3$, $CH_2CH=CH$, $CH=CHCH_2$, $CH(OH)CH=CH$ and $CH=CHCH(OH)$, Ar² is benzene, optionally substituted with 1–4 members selected from $R^4$, $OR^4$, $SR^4$ and halogen;

X represents a member selected from the group consisting of: $(CH_2)_2$, $CH=CH$ and 1,2-c-Pr, and Q is $CO_2H$.

4. A compound in accordance with claim 2 wherein:

Ar¹ is benzene unsubstituted or substituted in position 2 or position 4 or both relative to the point of attachment to W by a member selected from the group consisting of: OH, $OCH_2Ar^3$, $SCH_2Ar^3$, $OAr^3$, $SAr^3$ and $NR^2CH_2Ar^3$; and is optionally substituted at position 3 with one member selected from the group consisting of: OMe, $OCHF_2$ and lower alkyl;

Ar³ is benzene or thiophene, optionally substituted with $R^8$;

W is selected from the group consisting of: $CH_2OCH_2$, $(CH_2)_3$, $CH_2CH=CH$, $CH=CHCH_2$, $CH(OH)CH=CH$ and $CH=CHCH(OH)$;

Ar² is benzene, optionally substituted with $R^4$, $OR^4$, $SR^4$ or halo;

X is selected from the group consisting of: $(CH_2)_2$, $CH=CH$ and 1,2-c-Pr,

Q is $CONHSO_2ZAr^4$,

Z is a bond or $CH_2$, and

Ar⁴ is selected from the group consisting of: benzene, thiophene, 1,3,4-thiadiazole and naphthalene and is substituted with $R^8$.

5. A compound falling withing the following table:

TABLE I $(Ar^1-W-Ar^2-X-Q)$

| Ex | $Ar^1$ | W | $Ar^2$ | X | Q |
|---|---|---|---|---|---|
| 1 | 2-(BnO)-3-MePh | $(CH_2)_3$ | 1,2-Phe | $(CH_2)_2$ | $CO_2H$ |
| 2 | 2-(BnO)-3-MePh | $CH_2CH=CH$ | 1,2-Phe | $CH=CH$ | $CONHSO_2$-2-thienyl |
| 3 | 2-(BnO)-3-MePh | $CH=CHCH_2$ | 1,2-Phe | $CH=CH$ | $CONHSO_2$-2-thienyl |
| 4 | 2-((2-Cl-4-FPh)$CH_2O$)-3-$CF_3$Ph | $CH_2CH=CH$ | 1,2-Phe | $CH=CH$ | $CO_2H$ |
| 5 | 2-((2-Cl-4-FPh)$CH_2O$)-3-$CF_3$Ph | $CH=CHCH_2$ | 1,2-Phe | $CH=CH$ | $CO_2H$ |
| 6 | 2-(BnO)Ph | $CH_2CH=CH$ | 1,2-Phe | $CH=CH$ | $CO_2^-X^+$ |
| 7 | 2-(BnO)Ph | $CH=CHCH_2$ | 1,2-Phe | $CH=CH$ | $CO_2^-X^+$ |
| 8 | 4-(BnO)-3,5-$(MeO)_2$Ph | $CH_2CH=CH$ | 1,2-Phe | $CH=CH$ | $CO_2^-X^+$ |
| 9 | 4-(BnO)-3,5-$(MeO)_2$Ph | $CH=CHCH_2$ | 1,2-Phe | $CH=CH$ | $CO_2^-X^+$ |
| 10 | 2-(BnO)-5-AcPh | $CH_2CH=CH$ | 1,2-Phe | $CH=CH$ | $CO_2H$ |
| 11 | 2-(BnO)-5-AcPh | $CH=CHCH_2$ | 1,2-Phe | $CH=CH$ | $CO_2H$ |
| 12 | 2-(BnO)-3-(MeO)Ph | $CH_2CH=CH$ | 1,2-Phe | $CH=CH$ | $CO_2^-X^+$ |
| 13 | 2-(BnO)-3-(MeO)Ph | $CH=CHCH_2$ | 1,2-Phe | $CH=CH$ | $CO_2^-X^+$ |
| 14 | 4-(BnO)-3-(MeO)Ph | $CH_2CH=CH$ | 1,2-Phe | $CH=CH$ | $CO_2^-X^+$ |
| 15 | 4-(BnO)-3-(MeO)Ph | $CH=CHCH_2$ | 1,2-Phe | $CH=CH$ | $CO_2^-X^+$ |
| 16 | 2-(BnO O)-3-MePh | $CH_2CH=CH$ | 1,2-Phe | $CH_2$ | $CO_2^-X^+$ |
| 17 | 2-(BnO)-3-MePh | $CH=CHCH_2$ | 1,2-Phe | $CH_2$ | $CO_2^-X^+$ |
| 18 | 2-(BnO)-3-MePh | $CH_2CH=CH$ | 5-Cl-1,2-Phe | $CH_2$ | $CO_2^-X^+$ |
| 19 | 2-(BnO)-3-MePh | $CH=CHCH_2$ | 5-Cl-1,2-Phe | $CH_2$ | $CO_2^-X^+$ |
| 20 | 4-(BnO)-3-(MeO)Ph | $(CH_2)_3$ | 1,2-Phe | 1,2-c-Pr | $CO_2H$ |
| 21 | 2-(BnO)-3-MePh | $CH=CHCH_2$ | 4,5-$(MeO)_2$-1,2-Phe | $CH=CH$ | $CO_2H$ |
| 22 | 2-(BnO)-3-MePh | $CH_2CH=CH$ | 4,5-$(MeO)_2$-1,2-Phe | $CH=CH$ | $CO_2H$ |
| 23 | 3,4-(methylene dioxy)Ph | $CH=CHCH_2$ | 1,2-Phe | $CH=CH$ | $CO_2H$ |
| 24 | 3,4-(methylene dioxy)Ph | $CH_2CH=CH$ | 1,2-Phe | $CH=CH$ | $CO_2H$ |
| 25 | Ph | $CH=CHCH_2$ | 1,2-Phe | $CH=CH$ | $CO_2H$ |
| 26 | Ph | $CH_2CH=CH$ | 1,2-Phe | $CH=CH$ | $CO_2H$ |
| 27 | 2-(HO)-3-MePh | $CH=CHCH_2$ | 1,2-Phe | $CH=CH$ | $CO_2H$ |
| 28 | 2-(BnO)-3-MePh | $CH=CHCH_2$ | 1,2-Phe | $CH=CH$ | $CO_2^-X^+$ |
| 29 | 2-(BnO)-3-MePh | $CH_2CH=CH$ | 1,2-Phe | $CH=CH$ | $CO_2^-X^+$ |
| 30 | 2-((7-Cl-2-quinolinyl)$CH_2O$)-3-MePh | $CH=CHCH_2$ | 1,2-Phe | $CH=CH$ | $CO_2H$ |
| 31 | 2-((7-Cl-2-quinolinyl)$CH_2O$)-3-MePh | $CH_2CH=CH$ | 1,2-Phe | $CH=CH$ | $CO_2H$ |
| 32 | 2-(BnO)-3-MePh | $(CH_2)_3$ | 1,2-Phe | bond | $CO_2H$ |
| 33 | 2-(BnO)-3-MePh | $CH=CHCH_2$ | 1,2-Phe | bond | $CO_2^-X^+$ |
| 34 | 2-(BnO)-3-MePh | $CH_2CH=CH$ | 1,2-Phe | bond | $CO_2^-X^+$ |
| 35 | 2-(BnO)-3-MePh | $(CH_2)_3$ | 1,2-Phe | $CH=CH$ | $CO_2^-X^+$ |
| 36 | 2-(BnO)-3-(MeO)Ph | $(CH_2)_3$ | 1,2-Phe | $CH=CH$ | $CO_2^-X^+$ |
| 37 | 4-(BnO)-3-(MeO)Ph | $(CH_2)_3$ | 1,2-Phe | $CH=CH$ | $CO_2^-X^+$ |
| 38 | 4-(MeO)Ph | $CH_2CH=CH$ | 1,2-Phe | $CH=CH$ | $CO_2H$ |
| 39 | 4-(MeO)Ph | $CH=CHCH_2$ | 1,2-Phe | $CH=CH$ | $CO_2H$ |
| 40 | 3,4-$(MeO)_2$Ph | $CH_2CH=CH$ | 1,2-Phe | $CH=CH$ | $CO_2H$ |
| 41 | 3,4-$(MeO)_2$Ph | $CH=CHCH_2$ | 1,2-Phe | $CH=CH$ | $CO_2H$ |
| 42 | 2-(BnO)Ph | $CH(OH)CH=CH$ | 1,2-Phe | $CH=CH$ | $CO_2^-X^+$ |
| 43 | 2-(BnO)-3-MePh | $(CH_2)_3$ | 1,2-Phe | $(CH_2)_2$ | $CON^-X^+SO_2$-2-thienyl |
| 44 | 4-(BnO)-3-(MeO)Ph | $CH_2CH=CH$ | 1,2-Phe | $CH=CH$ | $CON^-X^+SO_2$-2-thienyl |
| 45 | 4-(BnO)-3-(MeO)Ph | $CH=CHCH_2$ | 1,2-Phe | $CH=CH$ | $CON^-X^+SO_2$-2-thienyl |
| 46 | 2-(BnO)-3-MePh | $CH_2$-1,2-c-Pr | 1,2-Phe | $CH=CH$ | $CO_2^-X^+$ |
| 47 | 2-(BnO)-3-MePh | 1,2-c-Pr-$CH_2$ | 1,2-Phe | $CH=CH$ | $CO_2^-X^+$ |
| 48 | 2-(BnO)-3-MePh | $CH(OH)CH=CH$ | 1,2-Phe | $CH=CH$ | $CO_2^-X^+$ |
| 49 | 2-(BnO)-3-MePh | $CH=CHCH(OH)$ | 1,2-Phe | $CH=CH$ | $CO_2H$ |
| 50 | 2-((2,6-$Cl_2$Ph)$CH_2O$)-3-MePh | $CH=CHCH(OH)$ | 1,2-Phe | $CH=CH$ | $CO_2H$ |
| 51 | 2-((2,6-$Cl_2$Ph)$CH_2O$)-3-MePh | $CH(OH)CH=CH$ | 1,2-Phe | $CH=CH$ | $CO_2H$ |
| 52 | 2-((4-FPh)$CH_2O$)-3-MePh | $CH_2CH=CH$ | 1,2-Phe | $CH=CH$ | $CO_2H$ |
| 53 | 2-((4-FPh)$CH_2O$)-3-MePh | $CH=CHCH_2$ | 1,2-Phe | $CH=CH$ | $CO_2^-X^+$ |

TABLE I-continued (Ar¹—W—Ar²—X—Q)

| Ex | Ar¹ | W | Ar² | X | Q |
|---|---|---|---|---|---|
| 54 | 2-((3,4-F₂Ph)CH₂O)-3-MePh | CH₂CH=CH | 1,2-Phe | CH=CH | CO₂H |
| 55 | 2-((3,4-F₂Ph)CH₂O)-3-MePh | CH=CHCH₂ | 1,2-Phe | CH=CH | CO₂⁻X⁺ |
| 56 | 2-((3,5-F₂Ph)CH₂O)-3-MePh | CH₂CH=CH | 1,2-Phe | CH=CH | CO₂H |
| 57 | 2-((3,5-F₂Ph)CH₂O)-3-MePh | CH=CHCH₂ | 1,2-Phe | CH=CH | CO₂⁻X⁺ |
| 58 | 2-((2,6-Cl₂Ph)CH₂O)-3-(HOCH₂)Ph | CH₂CH=CH | 1,2-Phe | CH=CH | CO₂H |
| 59 | 2-((2,6-Cl₂Ph)CH₂O)-3-(HOCH₂)Ph | CH=CHCH₂ | 1,2-Phe | CH=CH | CO₂H |
| 60 | 2-((2,6-Cl₂Ph)CH₂O)-3-MePh | CH₂CH=CH | 1,2-Phe | CH=CH | CO₂H |
| 61 | 2-((2,6-Cl₂Ph)CH₂O)-3-MePh | CH=CHCH₂ | 1,2-Phe | CH=CH | CO₂⁻X⁺ |
| 62 | 2-((4-CF₃Ph)CH₂O)-3-MePh | CH₂CH=CH | 1,2-Phe | CH=CH | CO₂H |
| 63 | 2-((4-CF₃Ph)CH₂O)-3-MePh | CH=CHCH₂ | 1,2-Phe | CH=CH | CO₂⁻X⁺ |
| 64 | 2-((4-(CHF₂O)Ph)CH₂O)-3-MePh | CH₂CH=CH | 1,2-Phe | CH=CH | CO₂H |
| 65 | 2-((4-(CHF₂O)Ph)CH₂O)-3-MePh | CH=CHCH₂ | 1,2-Phe | CH=CH | CO₂⁻X⁺ |
| 66 | 2-((4-CF₃Ph)CH₂O)-3-(HOCH₂)Ph | CH=CHCH(OH) | 1,2-Phe | CH=CH | CO₂H |
| 67 | 2-((4-CF₃Ph)CH₂O)-3-(HOCH₂)Ph | CH=CHCH₂ | 1,2-Phe | CH=CH | CO₂H |
| 68 | 2-((4-CF₃Ph)CH₂O)-3-MePh | CH=CHCH(OH) | 1,2-Phe | CH=CH | CO₂H |
| 69 | 2-(PhCH₂O)-3-(HOCH₂)Ph | CH=CHCH₂ | 1,2-Phe | CH=CH | CO₂H |
| 70 | 3-(PhO)Ph | CH₂OCH₂ | 1,2-Phe | CH=CH | CO₂⁻X⁺ |
| 71 | 2-(PhO)Ph | CH₂OCH₂ | 1,2-Phe | CH=CH | CO₂⁻X⁺ |
| 72 | 3-(BnO)Ph | CH₂CH=CH | 1,2-Phe | CH=CH | CO₂⁻X⁺ |
| 73 | 3-(BnO)Ph | CH=CHCH₂ | 1,2-Phe | CH=CH | CO₂⁻X⁺ |
| 74 | 2-(BnO)Ph | O(CH₂)₃O | 1,2-Phe | CH=CH | CO₂⁻X⁺ |
| 75 | 2-(PhCHMeO)-3-MePh | CH=CHCH₂ | 1,2-Phe | CH=CH | CO₂⁻X⁺ |
| 76 | 2-(PhCHMeO)-3-MePh | CH₂CH=CH | 1,2-Phe | CH=CH | CO₂H |
| 77 | 3-(PhO)Ph | CH=CHCH₂ | 1,2-Phe | CH=CH | CO₂⁻X⁺ |
| 78 | 3-(PhO)Ph | CH₂CH=CH | 1,2-Phe | CH=CH | CO₂⁻X⁺ |
| 79 | 3-Phbenzofuran-7-yl | CH=CHCH₂ | 1,2-Phe | CH=CH | CO₂⁻X⁺ |
| 80 | 3-Phbenzofuran-7-yl | CH₂CH=CH | 1,2-Phe | CH=CH | CO₂⁻X⁺ |
| 81 | Ph | CH=CHCH₂ | 1,2-Phe | CH=CH | CONHSO₂-2-thienyl |
| 82 | Ph | CH₂CH=CH | 1,2-Phe | CH=CH | CONHSO₂-2-thienyl |
| 83 | 4-(MeO)Ph | CH=CHCH₂ | 1,2-Phe | CH=CH | CONHSO₂-2-thienyl |
| 84 | 4-(MeO)Ph | CH₂CH=CH | 1,2-Phe | CH=CH | CONHSO₂-2-thienyl |
| 85 | 2-(BnO)-1-naphthyl | CH₂NHCO | 1,2-Phe | CH=CH | CO₂H |
| 86 | 2-((2-Cl-4-FPh)CH₂O)-3-MePh | CH₂CH=CH | 1,2-Phe | CH=CH | CO₂H |
| 87 | 2-((2-Cl-4-FPh)CH₂O)-3-MePh | CH=CHCH₂ | 1,2-Phe | CH=CH | CO₂H |
| 88 | 2-((2,4-F₂Ph)CH₂O)-3-MePh | CH₂CH=CH | 1,2-Phe | CH=CH | CO₂H |
| 89 | 2-((2,4-F₂Ph)CH₂O)-3-MePh | CH=CHCH₂ | 1,2-Phe | CH=CH | CO₂H |
| 90 | 2-((2,4,6-F₃Ph)CH₂O)-3-MePh | CH₂CH=CH | 1,2-Phe | CH=CH | CO₂H |
| 91 | 2-((2,4,6-F₃Ph)CH₂O)-3-MePh | CH=CHCH₂ | 1,2-Phe | CH=CH | CO₂H |
| 92 | 2-((2,6-Cl₂-4-FPh)CH₂O)-3-MePh | CH₂CH=CH | 1,2-Phe | CH=CH | CO₂H |
| 93 | 2-((2,6-Cl₂-4-FPh)CH₂O)-3-MePh | CH=CHCH₂ | 1,2-Phe | CH=CH | CO₂H |
| 94 | 2-((2,4-F₂Ph)CH₂O)-3-(CHF₂O)Ph | CH₂CH=CH | 1,2-Phe | CH=CH | CO₂H |
| 95 | 2-((2,4-F₂Ph)CH₂O)-3-(CHF₂O)Ph | CH=CHCH₂ | 1,2-Phe | CH=CH | CO₂H |
| 96 | 2-((4-FPh)CH₂O)- | CF₂CH=CH | 1,2-Phe | CH=CH | CO₂H |

TABLE I-continued

| | | (Ar¹—W—Ar²—X—Q) | | | |
|---|---|---|---|---|---|
| Ex | Ar¹ | W | Ar² | X | Q |
| 97 | 2-((4-FPh)CH$_2$O)-3-MePh | CH=CHCF$_2$ | 1,2-Phe | CH=CH | CO$_2$H |
| 98 | 2-((4-FPh)CH$_2$O)-3-MePh | (CH$_2$)$_3$ | 1,2-Phe | CH=CH | CONHSO$_2$-(4-i-PrPh) |
| 99 | 2-((4-FPh)CH$_2$O)-3-MePh | (CH$_2$)$_3$ | 1,2-Phe | CH=CH | CONHSO$_2$-(4-t-BuPh) |
| 100 | 2-((4-FPh)CH$_2$O)-3-MePh | CH$_2$CH=CH | 1,2-Phe | CH=CH | CONHSO$_2$-(4-(MeO)Ph) |
| 101 | 2-((4-FPh)CH$_2$O)-3-MePh | CH=CHCH$_2$ | 1,2-Phe | CH=CH | CONHSO$_2$-(2,3-Cl$_2$Ph) |
| 102 | 2-((4-FPh)CH$_2$O)-3-MePh | CH=CHCH$_2$ | 4-Cl-1,2-Phe | CH=CH | CONHSO$_2$-(5-Br-2-(MeO)Ph) |
| 103 | 2-((4-FPh)CH$_2$O)-3-MePh | (CH$_2$)$_2$S | 3-F-1,2-Phe | CH=CH | CONHSO$_2$-(2,3,4-Cl$_3$Ph) |
| 104 | 2-((4-FPh)CH$_2$O)-3-MePh | (CH$_2$)$_2$S | 6-CF$_3$-1,2-Phe | CH=CH | CONHSO$_2$-(5-F-2-MePh) |
| 105 | 2-((4-FPh)CH$_2$O)-3-MePh | (CH$_2$)$_2$S | 4,5-F$_2$-1,2-Ph | CH=CH | CONHSO$_2$-(2,5-Me$_2$Ph) |
| 106 | 2-((4-FPh)CH$_2$O)-3-MePh | (CH$_2$)$_2$SO$_2$ | 1,2-Phe | CH=CH | CONHSO$_2$-(4-CF$_3$Ph) |
| 107 | 2-((4-FPh)CH$_2$O)-3-MePh | (CH$_2$)$_2$SO$_2$ | 1,2-Phe | CH=CH | CONHSO$_2$-2-naphthyl |
| 108 | 2-((4-FPh)CH$_2$O)-3-MePh | CH=CHCH$_2$ | 3-F-1,2-Phe | CH=CH | CONHSO$_2$-(3-Cl-4-FPh) |
| 109 | 2-((4-FPh)CH$_2$O)-3-MePh | SO$_2$(CH$_2$)$_2$ | 1,2-Phe | CH=CH | CONHSO$_2$-(4-n-PrPh) |
| 110 | 2-((4-FPh)CH$_2$O)-3-(MeO)Ph | SO$_2$(CH$_2$)$_2$ | 1,2-Phe | CH=CH | CONHSO$_2$-(2-ClPh) |
| 111 | 2-((4-FPh)CH$_2$O)-3-(MeO)Ph | SO$_2$(CH$_2$)$_2$ | 1,2-Phe | CH=CH | CONHSO$_2$-(4-FPh) |
| 112 | 2-((4-FPh)CH$_2$O)-3-(MeO)Ph | S(CH$_2$)$_2$ | 1,2-Phe | CH=CH | CONHSO$_2$-(2-PhPh) |
| 113 | 2-((4-FPh)CH$_2$O)-3-(MeO)Ph | S(CH$_2$)$_2$ | 1,2-Phe | CH=CH | CONHSO$_2$-(2-CF$_3$Ph) |
| 114 | 2-((4-FPh)CH$_2$O)-3-(MeO)Ph | S(CH$_2$)$_2$ | 4-t-Bu-1,2-Phe | CH=CH | CONHSO$_2$-(4-Cl-2,5-Me$_2$Ph) |
| 115 | 2-((4-FPh)CH$_2$O)-3-(MeO)Ph | O(CH$_2$)$_2$ | 1,2-Phe | CH=CH | CONHSO$_2$-(2,5-Cl$_2$Ph) |
| 116 | 2-((4-FPh)CH$_2$O)-3-(MeO)Ph | O(CH$_2$)$_2$ | 1,2-Phe | CH=CH | CONHSO$_2$-(4-Br-2-(CF$_3$O)Ph) |
| 117 | 2-((4-FPh)CH$_2$O)-3-(MeO)Ph | O(CH$_2$)$_2$ | 1,2-Phe | CH=CH | CONHSO$_2$-CH$_2$Ph |
| 118 | 2-((4-FPh)CH$_2$O)-3-(MeO)Ph | (CH$_2$)$_2$O | 1,2-Phe | CH=CH | CONHSO$_2$-1-naphthyl |
| 119 | 2-((4-FPh)CH$_2$O)-3-(MeO)Ph | (CH$_2$)$_2$O | 4,5-F$_2$-1,2-Phe | CH=CH | CONHSO$_2$-(2-FPh) |
| 120 | 2-((4-FPh)CH$_2$O)-3-(MeO)Ph | (CH$_2$)$_2$O | 1,2-Phe | CH=CH | CONHSO$_2$-(2,4-Cl$_2$Ph) |
| 121 | 2-((4-FPh)CH$_2$O)-3-(MeO)Ph | (CH$_2$)$_3$ | 1,2-Phe | CH=CH | CONHSO$_2$-CH=CHPh |
| 122 | 2-((4-FPh)CH$_2$O)-3-(MeO)Ph | (CH$_2$)$_3$ | 1,2-Phe | CH=CH | CONHSO$_2$-(3,5-(CF$_3$)$_2$Ph) |
| 123 | 2-((4-FPh)CH$_2$O)Ph | (CH$_2$)$_3$ | 1,2-Phe | CH=CH | CONHSO$_2$-(2,5-Cl$_2$-3-thienyl) |
| 124 | 2-((4-FPh)CH$_2$O)Ph | (CH$_2$)$_4$ | 3-F-1,2-Phe | CH=CH | CONHSO$_2$-(3-BrPh) |
| 125 | 2-((4-FPh)CH$_2$O)Ph | (CH$_2$)$_4$ | 3-MeO-1,2-Phe | CH=CH | CONHSO$_2$-(2-BrPh) |
| 126 | 2-((4-FPh)CH$_2$O)Ph | (CH$_2$)$_4$ | 1,2-Phe | CH=CH | CONHSO$_2$-(2-NO$_2$Ph) |
| 127 | 2-((4-FPh)CH$_2$O)Ph | (CH$_2$)$_5$ | 1,2-Phe | (CH$_2$)$_2$ | CONHSO$_2$-(3-ClPh) |
| 128 | 2-((4-FPh)CH$_2$O)Ph | (CH$_2$)$_5$ | 1,2-Phe | (CH$_2$)$_2$ | CONHSO$_2$-(4-(CF$_3$O)Ph) |
| 129 | 2-HOPh | CH=CH(CH$_2$)$_2$ | 1,2-Phe | (CH$_2$)$_2$ | CONHSO$_2$-8-quinolinyl |
| 130 | 2-((4-FPh)CH$_2$O)Ph | CH=CH(CH$_2$)$_2$ | 5-(CF$_3$O)-1,2-Phe | (CH$_2$)$_2$ | CONHSO$_2$-(3,4-Cl$_2$Ph) |
| 131 | 4-((2,6-Cl$_2$-4- | CH=CH(CH$_2$)$_2$ | 3-F-1,2-Phe | (CH$_2$)$_2$ | CONHSO$_2$- |

TABLE I-continued

| | | (Ar$^1$—W—Ar$^2$—X—Q) | | | |
|---|---|---|---|---|---|
| Ex | Ar$^1$ | W | Ar$^2$ | X | Q |
| 132 | FPh)CH$_2$O)-3-MePh 2-((4-FPh)CH$_2$O)Ph | CH$_2$CH=CH | 1,2-Phe | (CH$_2$)$_2$ | (4-EtPh) CONHSO$_2$-(4-Cl-2-NO$_2$Ph) |
| 133 | 2-((4-FPh)CH$_2$O)Ph | CH=CHCH$_2$ | 4,5-F$_2$-1,2-Phe | CH=CH | CONHSO$_2$-(2-Cl-3-Br-5-thienyl) |
| 134 | 2-((4-FPh)CH$_2$O)Ph | CH$_2$CH=CH | 4,5-F$_2$-1,2-Phe | CH=CH | CONHSO$_2$-(3,4-(MeO)$_2$Ph) |
| 135 | 2-HOPh | CH=CHCH$_2$ | 4,5-F$_2$-1,2-Phe | CH=CH | CONHSO$_2$-(2,5-Cl$_2$-3-Br-4-thienyl) |
| 136 | 4-((4-FPh)CH$_2$O)-3-(MeO)Ph | CH$_2$CH=CH | 4,5-F$_2$-1,2-Phe | CH=CH | CONHSO$_2$-(4-Br-2,5-F$_2$Ph) |
| 137 | 4-((4-FPh)CH$_2$O)-3-(MeO)Ph | CH=CHCH$_2$ | 1,2-Phe | CH=CH | CONHSO$_2$-(5-(AcNH)-1,3,4-thiadiazol-2-yl) |
| 138 | 4-((4-FPh)CH$_2$O)-3-(MeO)Ph | CH$_2$CH=CH | 1,2-Phe | CH=CH | CONHSO$_2$-(2,3,4,5,6-F$_5$Ph) |
| 139 | 4-((2-Cl-4-FPh)CH$_2$O)-3-MePh | CH=CHCH$_2$ | 1,2-Phe | CH=CH | CONHSO$_2$-(2-CNPh)$_2$ |
| 140 | 2-((4-FPh)CH$_2$O)Ph | CH$_2$CH=CH | 4-F-1,2-Phe | CH=CH | CONHSO$_2$-(2-Cl-6-MePh) |
| 141 | 2-HOPh | CH=CHCH$_2$ | 1,2-Phe | CH=CH | CONHSO$_2$-(2,4,6-Me$_3$Ph) |
| 142 | Ph | CH$_2$CH=CH | 1,2-Phe | CH=CH | CONHSO$_2$-(2,3-Br$_2$-2-thienyl) |
| 143 | 2-((4-FPh)CH$_2$O)Ph | CH=CHCH$_2$ | 1,2-Phe | CH$_2$O | CONHSO$_2$-(4-NO$_2$Ph) |
| 144 | 2-((4-FPh)CH$_2$O)Ph | CH$_2$CH=CH | 1,2-Phe | CH$_2$O | CONHSO$_2$-(3,5-Cl$_2$Ph) |
| 145 | 2,4-((4-FPh)CH$_2$O)$_2$Ph | CH=CHCH$_2$ | 1,2-Phe | prop-1-yne-1,3-diyl | CONHSO$_2$-(5-Cl-2-thienyl) |
| 146 | 4-((2,4-F$_2$Ph)CH$_2$O)-3-(MeO)Ph | CH$_2$CH=CH | 1,2-Phe | CH$_2$O | CONHSO$_2$-(4-CF$_3$Ph) |
| 147 | 2-HO-3-MePh | CH=CHCH$_2$ | 1,2-Phe | CH$_2$O | CONHSO$_2$-(2,4-F$_2$Ph) |
| 148 | 2-((4-FPh)CH$_2$O)Ph | CH$_2$CH=CH | 4-F-1,2-Phe | 1,2-ethyne diyl | CONHSO$_2$-(4-ClPh) |
| 149 | 2-((4-FPh)CH$_2$O)Ph | CH=CHCH$_2$ | 1,2-Phe | 1,2-ethyne diyl | CONHSO$_2$-(3-CF$_3$Ph) |
| 150 | 4-HOPh | CH$_2$CH=CH | 1,2-Phe | 1,2-ethyne diyl | CONHSO$_2$-Ph |
| 151 | 2-((4-FPh)CH$_2$O)Ph | CH=CHCH$_2$ | 1,2-Phe | prop-2-yne-1,3-diyl | CONHSO$_2$-(5-Br-2-thienyl) |
| 152 | 2,4-((4-FPh)CH$_2$O)$_2$Ph | CH$_2$CH=CH | 1,2-Phe | 1,2-ethynediyl | CONHSO$_2$-Me |
| 153 | 2,4-((4-FPh)CH$_2$O)$_2$Ph | CH=CHCH$_2$ | 1,2-Phe | 1,2-c-Pr | CONHSO$_2$-(2,5-(MeO)$_2$Ph) |
| 154 | 6-((4-FPh)CH$_2$O)-2-naphthyl | CH$_2$CH=CH | 4-F-1,2-Phe | 1,2-c-Pr | CONHSO$_2$-(3-MePh) |
| 155 | 2-((4-FPh)CH$_2$O)Ph | CH=CHCH$_2$ | 1,2-Phe | 1,2-c-Pr | CONHSO$_2$-(4-MePh) |
| 156 | 4-HO-3-(MeO)Ph | CH$_2$CH=CH | 1,2-Phe | 1,2-c-Pr | CONHSO$_2$-n-Bu |
| 157 | 4-((4-FPh)CH$_2$O)-1-naphthyl | CH=CHCH$_2$ | 1,2-Phe | 1,2-c-Bu | CONHSO$_2$-(2-Cl-4-FPh) |
| 158 | Ph | CH$_2$CH=CH | 1,2-Phe | CH=CH | CONHSO$_2$-(2-MePh) |
| 159 | 2-((4-FPh)CH$_2$O)Ph | CH=CHCH$_2$ | 1,2-Phe | CH=CH | CONHSO$_2$-c-Pr |
| 160 | 2,4-((4-FPh) | CH=CHCH$_2$ | 1,2-Phe | CH=CH | CO$_2$H |

TABLE I-continued

| | | (Ar$^1$—W—Ar$^2$—X—Q) | | | |
|---|---|---|---|---|---|
| Ex | Ar$^1$ | W | Ar$^2$ | X | Q |
| 161 | 4-((2,4-F$_2$Ph)CH$_2$O)$_2$Ph CH$_2$O)-3-(MeO)Ph | (CH$_2$)$_3$ | 4-F-1,2-Phe | CH=CH | 1H-Tetrazol-5-yl |
| 162 | 2-((4-FPh)CH$_2$O)Ph | CH=CHCH$_2$ | 3-MeO-1,2-Phe | CH=CH | 1H-tetrazol-5-yl |
| 163 | 2,4-((4-FPh)CH$_2$O)$_2$Ph | CH=CHCH$_2$ | 1,2-Phe | CH=CH | 1H-tetrazol-5-yl |
| 164 | 4-HO-3-(MeO)Ph | CH=CHCH$_2$ | 1,2-Phe | 1,2-c-Pr | 1H-tetrazol-5-yl |
| 165 | Ph | CH=CHCH$_2$ | 1,2-Phe | (CH$_2$)$_2$ | 1H-tetrazol-5-yl |
| 166 | 2-((4-FPh)CH$_2$O)-3-(MeO)Ph | CH=CHCH$_2$ | 1,2-Phe | CH=CH | SO$_3$H |
| 167 | 2-((4-FPh)CH$_2$O)-3-MePh | (CH$_2$)$_3$ | 4-F-1,2-Phe | (CH$_2$)$_2$ | SO$_3$H | wherein X$^+$ represents a cation.

6. A compound in accordance with claim 5 wherein X$^+$ represents a cation selected from the group consisting of: ammonium, calcium, magnesium, potassium and sodium.

7. A pharmaceutical composition comprised of a compound in accordance with claim 1 in combination with a pharmaceutically acceptable carrier.

8. A method of treating or preventing an E prostaglandin mediated disease in a mammalian patient, comprising administering to said patient a compound in accordance with claim 1 in an amount which is effective to treat or prevent said E prostaglandin mediated disease.

9. A method of treating or preventing a prostaglandin mediated disease in accordance with claim 8 wherein the prostaglandin mediated disease is selected from the group consisting of:

Pain, fever, inflammation, rheumatic fever, symptoms associated with influenza or other viral infections, common cold, low back and neck pain, skeletal pain, post-partum pain, dysmenorrhea, headache, migraine, toothache, sprains, strains, myositis, neuralgia, synovitis, arthritis, degenerative joint diseases, (osteoarthritis), gout, ankylosing spondylitis, bursitis, burns, sunburns, pain following surgical and dental procedures.

10. A pharmaceutical composition comprised of a compound in accordance with claim 2 in combination with a pharmaceutically acceptable carrier.

11. A method of treating or preventing an E prostaglandin mediated disease in a mammalian patient, comprising administering to said patient a compound of in accordance with claim 2 in an amount which is effective to treat or prevent said E prostaglandin mediated disease.

12. A method of treating or preventing a prostaglandin mediated disease in accordance with claim 11 wherein the prostaglandin mediated disease is selected from the group consisting of:

Pain, fever, inflammation, rheumatic fever, symptoms associated with influenza or other viral infections, common cold, low back and neck pain, skeletal pain, post-partum pain, dysmenorrhea, headache, migraine, toothache, sprains, strains, myositis, neuralgia, synovitis, arthritis, degenerative joint diseases, (osteoarthritis), gout, ankylosing spondylitis, bursitis, burns, sunburns, pain following surgical and dental procedures.

* * * * *